US011114208B1

United States Patent
Thomas et al.

(10) Patent No.: US 11,114,208 B1
(45) Date of Patent: Sep. 7, 2021

(54) METHODS AND SYSTEMS FOR PREDICTING A DIAGNOSIS OF MUSCULOSKELETAL PATHOLOGIES

(71) Applicants: AIINPT, Inc, New City, NY (US); Sinju Thomas, New City, NY (US); Viji Mary Vergis, New City, NY (US)

(72) Inventors: Sinju Thomas, New City, NY (US); Viji Mary Vergis, New City, NY (US)

(*) Notice: Subject to any disclaimer, the term of this patent is extended or adjusted under 35 U.S.C. 154(b) by 0 days.

(21) Appl. No.: 17/093,473

(22) Filed: Nov. 9, 2020

(51) Int. Cl.
| | |
|---|---|
| *G16H 50/20* | (2018.01) |
| *G06K 9/00* | (2006.01) |
| *G16H 50/70* | (2018.01) |
| *G16H 70/60* | (2018.01) |
| *G16H 40/67* | (2018.01) |
| *G16H 50/50* | (2018.01) |
| *G16H 50/30* | (2018.01) |
| *G16H 10/60* | (2018.01) |
| *G16H 15/00* | (2018.01) |
| *A61B 5/00* | (2006.01) |
| *A61B 5/107* | (2006.01) |

(Continued)

(52) U.S. Cl.
CPC ........... *G16H 50/20* (2018.01); *A61B 5/0077* (2013.01); *A61B 5/1071* (2013.01); *A61B 5/1079* (2013.01); *A61B 5/1128* (2013.01); *A61B 5/4561* (2013.01); *A61B 5/7275* (2013.01); *G06K 9/00362* (2013.01); *G16H 10/20* (2018.01); *G16H 10/60* (2018.01); *G16H 15/00* (2018.01); *G16H 40/67* (2018.01); *G16H 50/30* (2018.01); *G16H 50/50* (2018.01); *G16H 50/70* (2018.01); *G16H 70/60* (2018.01)

(58) Field of Classification Search
CPC ........ G16H 50/20; G16H 40/67; G16H 70/60; G16H 50/50; G16H 10/60; G16H 15/00; G16H 50/30; G16H 50/70; G16H 10/20; A61B 5/0077; A61B 5/1071; A61B 5/1079; A61B 5/1128; A61B 5/4561; A61B 5/7275; G06K 9/00362
USPC .......................................................... 705/2
See application file for complete search history.

(56) References Cited

U.S. PATENT DOCUMENTS

| | | |
|---|---|---|
| 7,330,760 B2 | 2/2008 | Heruth et al. |
| 8,876,739 B2 | 11/2014 | Salarian et al. |

(Continued)

*Primary Examiner* — Michael Tomaszewski
*Assistant Examiner* — Rachael Sojin Stone

(57) ABSTRACT

Disclosed herein is a clinical decision support system for predicting a diagnosis of musculoskeletal pathologies, in accordance with some embodiments. Accordingly, the clinical decision support system may include a communication device, a processing device, and a storage device. Further, the communication device may be configured for transmitting questions to a first device and receiving responses corresponding to the questions from the first device. Further, the communication device may be configured for transmitting a prediction to a second device. Further, the processing device may be communicatively coupled with the communication device. Further, the processing device may be configured for analyzing the responses based on a knowledge repository and generating the prediction of a diagnosis of a musculoskeletal pathology using a machine learning model based on the analyzing. Further, the storage device may be communicatively coupled with the processing device. Further, the storage device may be configured for retrieving the knowledge repository.

16 Claims, 15 Drawing Sheets

(51) Int. Cl.
*A61B 5/11* (2006.01)
*G16H 10/20* (2018.01)

(56) References Cited

U.S. PATENT DOCUMENTS

| | | | |
|---|---|---|---|
| 9,154,739 B1 | 10/2015 | Nicolaou et al. | |
| 10,420,982 B2 | 9/2019 | Aragones et al. | |
| 10,783,632 B2* | 9/2020 | Fan | A61B 5/7275 |
| 2002/0184065 A1* | 12/2002 | Menard | H04L 43/16 |
| | | | 709/224 |
| 2004/0122708 A1* | 6/2004 | Avinash | G16H 70/00 |
| | | | 705/2 |
| 2004/0122719 A1* | 6/2004 | Sabol | G06Q 10/06315 |
| | | | 705/7.13 |
| 2004/0122790 A1* | 6/2004 | Walker | G16H 30/40 |
| 2007/0118399 A1* | 5/2007 | Avinash | G16H 10/60 |
| | | | 705/2 |
| 2014/0095189 A1* | 4/2014 | Holmes | H04L 29/08234 |
| | | | 705/2 |
| 2014/0276095 A1 | 9/2014 | Griggs | |
| 2017/0372027 A1* | 12/2017 | Apte | G16B 20/00 |
| 2018/0184947 A1 | 7/2018 | Richards et al. | |

\* cited by examiner

METHODS AND SYSTEMS FOR PREDICTING A DIAGNOSIS OF MUSCULOSKELETAL PATHOLOGIES

FIELD OF THE INVENTION

Generally, the present disclosure relates to the field of medical and laboratory equipment. More specifically, the present disclosure relates to methods and systems for facilitating for predicting a diagnosis of musculoskeletal pathologies.

BACKGROUND OF THE INVENTION

Existing techniques for predicting a diagnosis of musculoskeletal pathologies are deficient with regard to several aspects. For instance, current technologies do not provide a questionnaire to the patient for establishing a clinical decision support system. Further, current technologies and/or medical systems use the identification of tissue at fault for diagnosis and to establish a treatment. However, isolating a particular tissue to diagnose a musculoskeletal condition with mechanical pain is difficult or in some cases virtually impossible. Moreover, current technologies do not provide value-based patient-centered care to the patient.

Therefore, there is a need for improved methods and systems for predicting a diagnosis of musculoskeletal pathologies that may overcome one or more of the above-mentioned problems and/or limitations.

BRIEF SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a clinical decision support system for predicting a diagnosis of musculoskeletal pathologies, in accordance with some embodiments. Accordingly, the clinical decision support system may include a communication device, a processing device, and a storage device. Further, the communication device may be configured for transmitting a plurality of questions associated with a musculoskeletal system of a body to at least one first device. Further, the plurality of questions may be formulated based on one or more of an affected region, a patient complaint, a clinical manifestation, and a dermatomal pattern of the body. Further, the communication device may be configured for receiving a plurality of responses corresponding to the plurality of questions from the at least one first device. Further, the plurality of responses may include at least one indication of musculoskeletal pain and/or a clinical presentation (signs) and/or a symptom associated with at least one portion of the body. Further, the communication device may be configured for transmitting a prediction to at least one second device. Further, the processing device may be communicatively coupled with the communication device. Further, the processing device may be configured for analyzing the plurality of responses based on a knowledge repository. Further, the processing device may be configured for generating the prediction of a diagnosis of at least one musculoskeletal pathology using at least one machine learning model based on the analyzing. Further, the storage device may be communicatively coupled with the processing device. Further, the storage device may be configured for retrieving the knowledge repository.

Further disclosed herein is a method for providing clinical decision support for predicting a diagnosis of musculoskeletal pathologies, in accordance with some embodiments. Accordingly, the method may include transmitting, using a communication device, a plurality of questions associated with a musculoskeletal system of a body to at least one first device. Further, the plurality of questions may be formulated based on one or more of an affected region, a patient complaint, a clinical manifestation, and a dermatomal pattern of the body. Further, the method may include receiving, using the communication device, a plurality of responses corresponding to the plurality of questions from the at least one first device. Further, the plurality of responses may include at least one indication of musculoskeletal pain and/or a clinical presentation (signs) and/or a symptom associated with at least one portion of the body. Further, the method may include retrieving, using a storage device, a knowledge repository. Further, the method may include analyzing, using a processing device, the plurality of responses based on the knowledge repository. Further, the method may include generating, using the processing device, a prediction of a diagnosis of at least one musculoskeletal pathology using at least one machine learning model based on the analyzing. Further, the method may include transmitting, using the communication device, the prediction to at least one second device. Additionally, in some embodiments, the method may include transmitting, using the communication device, a summary to the at least one first device. Further, in some embodiments, the summary may include the prediction.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTIONS OF THE INVENTION

Figure 1:
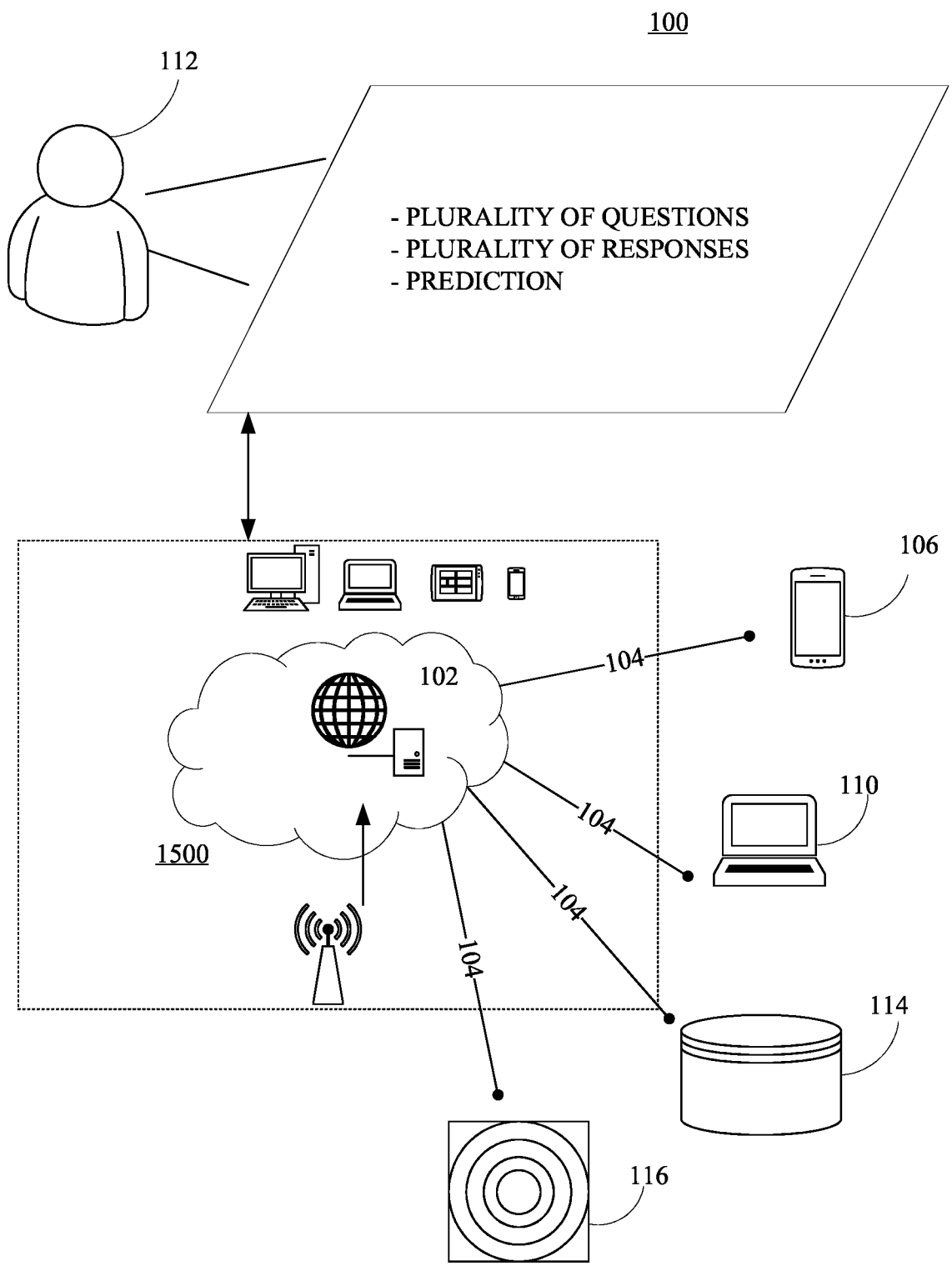
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of methods and systems for predicting a diagnosis of musculoskeletal pathologies, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor and at least one actuator. Examples of the one or more client devices and/or the server computer may include, a desktop computer, a laptop computer, a tablet computer, a personal digital assistant, a portable electronic device, a wearable computer, a smart phone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice based interface, gesture based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third party database, public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role based access control, and so on.

Further, one or more steps of the method disclosed herein may be initiated, maintained, controlled and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable data (e.g. username, password, passphrase, PIN, secret question, secret answer etc.) and/or possession of a machine readable secret data (e.g. encryption key, decryption key, bar codes, etc.) and/or or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smart-card with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data, and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview:

The present disclosure describes methods and systems for predicting a diagnosis of musculoskeletal pathologies. Further, the disclosed system may include a Clinical Decision Support System (CDSS). Further, the CDSS may include a comprehensive screening software designed for triaging spinal pathologies over a secured web-portal or patient portal. The software may be designed to capture high-quality, patient-centric data in a standardized way that empowers clinical reasoning to deliver optimal care. Further, a machine learning model of the CDSS fosters the transformation of the current healthcare system into a 'learning health system' with a salutary effect on population health.

Musculoskeletal care varies widely between different disciplines of the medical profession creating a lot of confusion for the patient. Though a marked variability exists with care in interprofessional and intraprofessional domains, patients and their stories remain the same. To provide value-based, patient-centered care, a newer model of Spine care delivery needs to be in place. Further, disclosed CDSS may be initiated by patients themselves with the deliverables within the clinical workflow. The result may be more detailed first-hand information for better clinical reasoning and thereby a patient-specific treatment plan. A goal will be to prevent overutilization of resources, psychological distress, and productivity loss through an evidence-based program. The machine learning model provides better utilization of clinicians skilled time to have face-to-face interaction with patients. The disclosed CDSS may utilize advancements in science to revamp the age-old practice of medical history by assimilating clinical data for refined clinical reasoning and predictions from a patient self-administered questionnaire. The disclosed CDSS may exploit the computational power to bring the world of clinical knowledge to actionable decisions using deductive reasoning to deliver the best possible care on time. A basic premise is that the intelligent design of health information systems can unite clinical practice with clinical research and contribute powerfully to a 'learning healthcare system', with everyone learning from his or her practice base. The disclosed CDSS may facilitate achieving better patient health individually and generally across all patients. Further, achieving better patient health individually may require the current health system to capture the power of learning healthcare systems. Further, the current health system may capture the power of learning healthcare systems through the integration of Machine Learning to the CDSS without disrupting the current clinical workflow. The integration of the disclosed CDSS to practice may create a more effective learning healthcare system that can serve as a model even outside the system paving the way for better health care delivery. In some instances, the disclosed CDSS may not recommend any particular treatment option but rather suggest one or more clinical diagnosis based on the medical history for better clinical reasoning. Consistency in the accuracy of predictions may pave the way for better design care pathways in the musculoskeletal world. Alternatively, in some instances, the disclosed CDSS may provide one or more treatment options.

The United States' spending on healthcare is notorious worldwide. With 18% of the nation's GDP spent on healthcare, our spending far exceeds that of any other country and is projected to rise even further to a level of 20%, reaching a total of $5.7 trillion by 2026. In 2016, the US spent 390.9 billion dollars on musculoskeletal disorders, of which the cost associated with the category of neck and back alone (not the entire spine) was a staggering $134.5 billion. The combined spending on diabetes, other endocrine disorders, urogenital, and blood pathology is still 81.8 billion dollars less than this. Cardiovascular disease, as a category, only ranks third in position with an estimated US $255.1 billion in healthcare spending [6].

The musculoskeletal field is periodically enriched with new diagnostic and treatment approaches, which get integrated into the treatment of normal aches and pains long before we weigh the benefits against harms. A marked proliferation of innovative technologies has resulted in an exponential rise in the cost of musculoskeletal care with no overall discernible improvement in health outcomes. With the emergence of clinical specialties, the so-called 'precise and targeted care' has led to redundancy, longer waiting periods, overdiagnosis, and overtreatment, further paving way for chronic stages and dependency. A huge erosion in clinical quality occurred when the system shifted gears to 'image-focused' healthcare delivery as opposed to understanding the individual patients and their challenges.

Pain cannot be visualized from the standpoint of tissue pathology alone directing the treatment to the involved tissue but needs to be viewed from the perspective of the patient who is experiencing the same. Even though there are numerous guidelines to streamline care for spine-related pathologies, implementation and changing clinician behaviors are still a challenge resulting in a significant rise in opioid prescription (further facilitating dependency, addiction, and mortality), and failed surgeries. The result is an astonishing 660% increase in healthcare expenditure. Spinal imaging has been inappropriately utilized, as well as other practices including additional investigation, referral, and potentially invasive procedure, that for most represent low-value care. Given these considerations and the fact that spine care is being identified as a global burden, it is crucial to find a change in treatment delivery that is sustainable and transferable.

The challenges of overutilization, greater demand, inefficiencies resulting in poor productivity, and discrepancy in healthcare service delivery can be addressed to a vast extent through the judicial integration of Artificial Intelligence, Machine Learning, and Computer Vision. It is a known fact that the healthcare industry lags behind other industries in the implementation of the same and the musculoskeletal field, in particular, is slacking far behind the race. It is only by embracing these technologies in this new data-centric era of productivity that can we provide 'patient-centric' and 'value-based' healthcare. A newer model of care delivery which is backed up with evidence needs to replace the current system and satisfies all parties—patients, care providers, policymakers, and of course the insurance companies would be disruptive and timely.

For a variety of reasons, the demand for treatment is increasing and this only exacerbates the problems and challenges described above. If healthcare stays on the current trajectory, inefficient and poor value practices may be expected to proliferate. These problems can be addressed to a large extent through the judicial integration of artificial intelligence, machine learning, and computer vision. It is a known fact that the healthcare industry lags behind others in the implementation of these technologies and the musculoskeletal field lags even further.

With the idea of addressing all the complexities in the healthcare system that have direct and indirect influence in the healthcare delivery, the disclosed Clinical Decision Support System (CDSS) may utilize utilizing a machine learning algorithm for triaging spine pathologies. The approach is 'patient-centric', or even better—'person-centric' providing 'value-based' healthcare with precision medicine in a simple, inexpensive, and reproducible process to set a new standard in healthcare delivery.

The disclosed system utilizes the patient's self-administered or clinician gathered information to guide the diagnosis, screen for sinister pathologies, and to narrow down the examination. A 10-12 minute web-based interactive tool makes patients more knowledgeable and involved in their care process. The CDSS provides clinicians with patient-specific information that is filtered and presented in a structured manner even before they see their patients, allowing improved clinical decision-making. Further, the disclosed CDSS may deliver the right information at the right time to the right provider in the right format, seamlessly within the provider's workflow or decision-making process adds value in the care delivery.

Currently, medical history taking is occupying a back seat as clinicians are losing much time in listening to patients' prolix accounts of sufferings, irrelevant details, opinions from previous consultations, or self-diagnosis through a web search. This has dehumanized healthcare with more time spent on discussions of investigative procedures and planning of future treatments. It further helps in building rapport by re-telling patients' versions in a more structured way which will help in establishing trust and respect in the initial encounter itself. In simple terms, the disclosed CDSS is a digital version of medical history taking and clinical reasoning which is synchronically working along with the human brain. This makes the person trusting less of the treatments they have been offered. It is vivid that the current healthcare system is investigation driven rather than viewing the patient as a person and determining a tissue at fault rather than considering the person as a whole.

Cognitive research shows that a human utilizes five to nine facts in a single decision-making instance [7]. Further, the CDSS facilitates narration of facts which are 'clinical pearls' for making more informed decisions. The CDSS humanizes healthcare allowing patients to tell their version of the story uninterrupted. In simpler terms, the disclosed CDSS is a digital version of medical history taking and clinical reasoning utilizing best practices of an idealized skilled clinician.

Clinicians' judgments are often rooted in their training, schools of thought, experience levels, skill sets, and oftentimes their work demands and hence cannot be objectively measured or quantified. The heterogeneity of treatment for spine care is evidenced in a recent study, which showed 69% disagreement among spinal surgeons on how they view recurrent lumbar disk herniation and 75% variation with lower back treatment in general [8]. Irrespective of their background clinicians and researchers unequivocally admit patient sourced 'soft data' to be unique, relevant, and powerful in decision making as long as it is obtained in a structured, refined manner and can be analyzed to make an appropriate and targeted clinical diagnosis. The need for evidence-based clinical tools in making the 'soft data', 'hard' is critical to empower the clinician's decision-making skills.

The emergence of powerful Machine Learning algorithms that work seamlessly in conjunction with the human brain and are capable of identifying intricate and potentially undetected patterns to create predictive models could be adopted into the clinical flow. Once the model is tested and proved viable, that platform could serve as legitimate clinical decision-making and triaging tool in spine care by serving as a reliable source for improving clinician performance and promoting appropriate, efficient care in this era of person-centered, value-based healthcare delivery.

Numerous researches consistently state that 75-83% of clinical diagnoses in outpatient settings can be obtained from a good history through the hands of an experienced skilled clinician [12]. From the business point of the healthcare industry, with value-based care yet to be implemented in outpatient settings, providers are paid more if they overuse resources and if they provide poor care leading to rework. They are reimbursed more for technical and episodic tasks and little for cognitive, coordinative work. In the face of technological upsurge, the medical system is more tweaked to investigation based treatment than patient-centered care to 'identify and isolate' tissue or structure at fault in each episodic care. Health professionals rely too much on investigative procedures to label a person and or to rationalize patients' complaints who are also seeking a 'definite answer' for their complaints through the reports generated. An interesting finding from a study that compared low-value care between Medicare and commercial insurances was, that there is no difference between both when it comes to delivering or avoiding low-value care. These findings underline the fact that low-value care is non-discriminate between payer types and has become a 'cultural norm' among providers in the US healthcare industry contributing to the overuse, underuse, and misuse of medical care.

By and large, health professionals are passionate about doing the right thing and are attempting to provide care for patients but with the crush of information, a plethora of new technologies, increased regulatory oversight, an aging population, and heightened consumer awareness and expectations have all contributed to the disorganization, fragmentation, and discontinuity of patient care. The making of a medical diagnosis depends on three things: the history obtained from the patient, the signs noticed (elicited) on physical examination based on history, and the results of investigative studies to correlate with the pattern recognized to confirm a treatment diagnosis. An extensive study on how the history taking has evolved has identified (that the clinical assessment has) three different phases which are in the sequence of occurrence and significance: the first dominated by the taking of the patient history; the second, by physical examination; and the third, by technology. Unfortunately, in the surge of providing 'targeted care,' the sequence of importance has reversed with the least priority given to the person and their story.

The process of clinical assessment thus produces two histories: a superficial, chaotic story presented by the person who is living in the story—patient history, and a deep, 'true' history revealed by the skill of the clinician—the clinician history—re-telling the story in a more structured by teasing out 'facts' in a scientific way to make more sense to anyone who reads it. The second history determines the course of treatment and plan of care as that becomes the formal version of clinical documentation as patient records. This is never simply equivalent to the patient's story rather a narration of the clinician's perspective through their clinical eyes. It is always subject to a clinician's skepticism, interpretation of biomedical knowledge, bias by experience, and skill. In simpler terms, it may be a script of what the observer thought he saw, perhaps even what he wanted to see and hoped to do. This version becomes the main element of the business of medical practice. With as many as over a dozen healthcare providers per patient, the kind of 'education' can be contradicting and biased. Various factors like the clinician education and or training, as well as the stereotyping of patient's complaints and concerns to their experience, creates (leads to) confusion and fear in patients. To alleviate the uncertainties demands expensive investigative procedures that do not influence care plans but to add more complexities with the false positives. Each patient, their story, and the disease process are unique. It is essential to understand those characteristics and differences to deliver the most appropriate effective care. Stereotyping and biases by itself will lead to misdiagnosis and inappropriate plan of care and overutilization of healthcare resources.

"Every patient contains truth. He will proffer the data on which diagnosis rests. The doctor must adopt a conscious humility, not towards the patient but towards the truth contained within."—James Cyriax The patient's story is of value only in the hands of an experienced, expert clinician who could analyze it in much the same way as he did the objective signs of physical examination. The patient is the sufferer and a witness to his disease and as such his reliability must be assessed and judged. The clinician needs to be both detective and judge and to use his knowledge of human nature to come to a verdict. There are such things as "facts," but patients can be relied on only for feelings and not for ideas (of their disease). The clinician must use techniques, usually forensic and legal, to get the "facts" from an unreliable witness. It is widely recognized by experienced clinicians that a skillfully taken history, with a careful analysis of the chief complaints and of the course of the illness, will more frequently than not indicate the probable diagnosis, even before a physical diagnosis is done or with any investigative studies.

"In God we trust, but everyone else brings data."—Nikolai Bogduk.

The "facts" in the patient narration would be revealed only if the clinician took control of the history; it must not be a passive experience. A conscious effort must be utilized to lead the patient to present. The "art of history-taking" is pivotal as a ripe experience is a prerequisite (requisite) to utilize the history in making a diagnosis. History-taking was therefore a skill that required training, instruction, and expertise. The clinician needed to demonstrate tact, patience, and diplomacy in establishing a future patient-practitioner rapport as it could have a therapeutic function. Only individuals with great inter personal skills can give the patient history a utility and value. Without any doubt, history is the most important single factor in arriving at a diagnosis. Further, Therapha may exploit computational power to unlock time and mental space for clinicians to focus on the human aspects (empathy and patient interaction) of healthcare.

Further, the disclosed system may include a Clinical Decision Support System (CDSS) for spine triage utilizing a machine learning algorithm.

Further, the CDSS is built by skillfully planned questions to create a feel for virtual interaction with the prospective clinician by incorporating the sophistication of information technology with evidence, experience, and expertise in spine care. Utmost care is taken in designing the CDSS so that the uninterrupted story patient 'wants to share' is shared and the story each clinician would 'like to hear' is 'heard'. Both parties mutually agree upon the structured version to pave the way for a well-informed decision-making process. Diagnoses are determined based on the recognition of patterns from history taking which are further verified and confirmed through various physical examinations and later investigations if ambiguity arises. Upon completion of the questionnaires, Therapha delivers a comprehensive clinical summary with actionable recommendations to the patients. At the clinician's end—the clinical summary is ready to be automated for documentation along with a differential diagnosis, for the clinician to make further decisions. Hence, deliverables (such as the clinical summary) are in fact similar to a nutrition label, which simply explains how the tool derived its conclusion and will further satisfy the concerned explain ability of the tool (17).

Changing healthcare delivery (practice patterns) is much more difficult even with the introduction of new evidence. Research suggests it can take almost 20 years for a major new scientific (biomedical) knowledge to achieve geographically widespread acceptance and is directly associated with the inability of clinicians in practice to stay current [7]. This variation in the deployment of new medical knowledge reflects in variation in clinical practice as well. In 80 to 90 percent of cases, practicing clinicians can have legitimate differences of opinion about what is the best line of management, which is reflected vividly in actual practice.

The disclosed CDSS is not disruptive to the current workflow or the model of care (practice pattern) yet disruptive by its very nature of implementation and how efficient it is in the screening, decision making, and documentation. The algorithmic approach in Machine Learning works with pattern identification and matching versus the traditional subjective recall which relies on rate estimation. Anyone can ask questions or listen but asking the right (relevant) questions at the right time in the right manner (empathy) needs skill, knowledge, experience, and (clinical reasoning) understanding of the given context (along with patient ears). The same is achieved through this patient-self-administered questionnaire grounded in the principle of getting the right information to the right member of the healthcare team—including the patient—at the right time during the workflow or decision-making process.

The disclosed CDSS aims to triage spine related pathologies by identifying patterns, follow algorithmic approaches to develop and define care pathways, to predict risk, and make a differential diagnosis for the clinician to decide upon. The disclosed CDSS classifies spine pathologies into various subgroups along with conventional pathoanatomical models whenever it's applicable as spine pathologies have a significant biopsychosocial effect in the recovery and prognosis causing that model alone to fail over and over. The supervised Machine Learning model recognizes patterns just as a clinician makes decisions—and it relearns, refining its accuracy over time as it ingests greater amounts of information. The highlight of the disclosed CDSS is the active role of the patient to make it 'person-centered' and the clinician gets a second look to obtain more precise prediction making this tool to be a true decision 'support' system. This state-of-the-art technology is revamping the age-old practice of medical history by assimilating clinical data, identifying intricate and potentially undetected patterns to refine clinical reasoning and to create predictive models from a patient self-administered questionnaire. The disclosed CDSS is designed as a virtual chat with their prospective clinician mimicking when they are on their one-on-one visit. This virtual interview prepares the patient well as they are more organized with their illness history. The system provides better utilization of clinicians skilled time to have face-to-face interaction with patients and can target their examination to the prompts the CDSS generated. The current version is a stand-alone system and is not disruptive to the clinical workflow, hence holds better usability and integration to any electronic health records.

Unlike most other Machine learning models, the system is transparent and leaves no challenge to use this tool clinically. The collected information from the person creates a 'digital twin' for the ease of identifying them with what is fed in the database—knowledge repository, which is the brain of the algorithm where all the clinical reasoning happens to statistically weigh (in and out) for ranking hypothetical diagnosis. The screening tool incorporates the Machine Learning principle multivariate analysis of patient-reported clinical features, allowing each of them to contribute towards the overall picture (diagnosis) and establish the highest degree of correlation between those variants (for comparing against what's in the knowledge repository to find the closest matching diagnosis) in the generation of a clinical hypothesis which a human brain would have difficulty matching.

The system incorporates numerous clinical guidelines to establish linkage between patterns of independent variables (signs & symptoms) which a human brain might have missed or couldn't identify. The transparency in weighing the data to conclude makes it easy to comprehend how the system has arrived at a prediction or flagged out an alert. Based on this understanding, the clinician can then determine whether he should override the recommendations given by the CDSS or not. Unlike other Machine Learning tools, the principle behind the functioning of the disclosed system is transparent as the logic is easily understood and reproducible in a consistent manner to add credibility. Further, the highlight of this clinical decision support system is that there is no learning curve involved in any participating players, i.e., either the patients themselves or the clinician and doesn't require any space-occupying expensive equipments.

The CDSS is built upon a systematically organized, unbiased, uninterrupted, detailed first-hand report of patient history deliberately untapped by the current system and is embedded 'within-the-loop' to enhance the patient experience. It is designed to capture high-quality, patient-centric data in a standardized way, empowers the clinical reasoning to deliver optimal care, and further facilitates research (prospective and retrospective) and outcome-driven education. The tool identifies comorbidities, detects sinister pathologies through guideline-based screening, highlights risk factors and or severity, prior treatments, and their effects—leading to ease in diagnosis and avoids duplication of failed prior treatments and procedures. Since the patient self-reports, the data is more detailed and complete; the system has the potential to verify its relevance which can further be substantiated by the clinician when required.

The CDSS is integrated without disrupting the traditional clinical workflow and hence would be an ideal platform for incorporating research into everyday practice without being disruptive. It facilitates guideline-based treatments and incorporates clinical prediction rules effectively. Therapha™ (an exemplary embodiment of the CDSS disclosed herein) has layered the sensitivity of minor complaints by bundling them to generate a Clinical Prediction Rules which detects and amplifies the necessity or urgency of medical attention when required. Meantime, there is the provision to review any or all sensitive information for the clinician to make the final call. It prepares the clinician on how safe it is to proceed with the evaluation of the patient even before they see them in person and also recommends a need for a multidisciplinary approach when required for efficient and effective care delivery. The tool increases the value of care by providing better-quality results in a more efficient manner making it a win-win for all parties involved.

The disclosed CDSS has a significant role in clinical reasoning, actionable decision making, and optimal care delivery. Gathering patient-specific information will sharpen the clinical reasoning, target the examination—leading to informed decision making and patient-specific treatment plan. More detailed patient-centric documentation of 'refined data' further facilitates accurate analysis and prediction. Machine learning will reinvent clinicians'roles giving them more time to focus on valued-care.

Further, the disclosed CDSS may facilitate future research and education. The data without noises create a model for (health professional) education and (clinical) research. The data collected would be very detailed, documented appropriately for clinical practice and research purposes without the clinician investing his skilled time for clerical work. (Oftentimes, clinicians are overburdened by their dual-role of the dutiful obligation of record entry to EHR (for clinical, research, and or legal purposes) obstructing their professional obligations to deliver the best possible care for the well-being of patients.

Further, the disclosed CDSS may be considered as a comprehensive screening software designed to identify patients with high risk or those who require medical attention over a secured web portal or patient portal. Thus, CDSS would be a great addition to the care delivered via telehealth platforms. There is minimal or no adaptation required as the system is well within the workflow and can be easily integrated into any EHR making the system more appealing.

Further, the disclosed CDSS may facilitate the optimal utilization of resources. Further, the disclosed CDSS will be able to reduce the patient visit length reduction, incorporation of various risk predictors, specialist care can be provided or directed remotely, more personalized diagnosis and treatment, reduce overutilization of resources, readily available to integrate to any EHR platforms.

Because of the 'Patient-centered and Shared decision making' nature of this tool, patients are more accountable to their healthcare delivery by having a better understanding and adherence to treatment and self-management strategies. Since patients become active participants in this care delivery model, the recovery would be faster which further facilitates lesser utilization of resources and increased overall satisfaction. This will add value and 'care' back to current healthcare delivery. Patients would be more satisfied as the decisions made are based on their input, expert knowledge, and experience of the clinician along with the support of advanced technology.

The disclosed system is an aide in clinical evaluation and decision making as the whole process is not taking away one-on-one time from the patient-clinician team but rather adding more value to it. The tool will help clinicians in acquiring a comprehensive understanding of the patient and their story. Further, an effective and respectful clinical examination will facilitate delivering individually tailored management and coping strategies. One factor which is common across different approaches in treatment is the patient and his story.

The system doesn't demand any levels of computer literacy as it runs on any device with internet capability delivered even via a text message to open a chat session format in smart devices. The disclosed CDSS can function as a standalone utility or can very well integrate into any EHR platforms as a plugin.

The CDSS is developed by meticulously integrating decades of research and evidence-based practice to digitize age-old patient history taking processes. The disclosed Machine Learning tool has tactfully incorporated various 'Guideline Based Practices' and 'Clinical Prediction Rules' to produce quantifiable outcomes which otherwise would have been stand-alone, time-consuming utilities in clinical practice. The disclosed system further establishes linkage or association between independent variables (signs and symptoms) which a human brain might have missed, couldn't identify, or recognize as a pattern. The ultimate goal of the disclosed Clinical Decision Support System is to exploit the advancements in computational power to bring the world of clinical knowledge to actionable decisions using deductive reasoning and thereby deliver the best possible care on time.

The disclosed CDSS can be easily transferred to current practice without any change in workflow and adds further credibility by making the process more patient-centered and collaborative. This implementation of the existing workflow leads to the narrowing of the knowledge-to-practice gap. Recalling all the amount of medical knowledge gained and practiced over the years is difficult. To stay abreast of the recent advancements and research in the same field to incorporate into daily clinical practice is humanly impossible. Moreover, taking a wide and detailed history-taking is time-consuming and our medical system is more tweaked to investigation based treatment than patient-centered care. The disclosed system would be a perfect launching pad to integrate clinical prediction rules and guideline-based treatments into everyday clinical practice. This 'conspicuous way' of assimilation will be more instrumental in changing clinician behavior than passive educational integration.

Subjective history questions or self-reported items are commonly used to triage the patient with musculoskeletal symptoms such as, for example, spine, low back pain, and related leg symptoms. However, the value of patient self-administered questionnaires in establishing a clinical decision support system in Spine related pathology has never been attempted. Even though various forms of Clinical decision support tools have been around in the medical field for years none of them are addressing 'Pain'—especially Musculoskeletal pain. The physical impairment which is often coupled with the biopsychosocial model complicates the diagnosis and thereby the recovery. The disclosed CDSS will be the first of its kind in the Musculoskeletal domain and first to be initiated and integrated into the workflow.

The disclosed CDSS is intuitively designed to create a perception of patients having a chat with their 'prospective' healthcare provider. The patient can initiate and complete the task at their convenience, the questionnaires are very detail-oriented—leaving no stones unturned resulting in a more precise 'illness script' which is delivered in clinical note format for the clinician or anyone who wants to have access to the patient history saving even more skilled time on documentation. The result is generated by pattern recognition for a 'biomedical knowledge' in the Knowledge Repository Utilizing a Supervised Learning Algorithm.

The disclosed system is designed with a novel patient-centric, data-rich, feedforward information to an environment with real-time actionable feedback in the form of decision making and will aid in population health. It facilitates a collaborative healthcare delivery model for the patient and provider where the patient has an active role in their care. Also, it instills the principles of accountability, care coordination, expectation setting, incentive alignment, and patient-centered focus while ensuring innovation, quality, safety, and value in health care.

Initiated by the patient or in conjunction with their clinician during his initial visit where the clinician initiates the process by running the program along with the patient, and its ready availability at the initial point of contact, the disclosed CDSS is not disrupting the clinician workflow but will further facilitate the mantra of "Right care at right time". This Machine learning model differs significantly from the old one-doctor, one-patient, one-exam-room, paper-record model. Clinical decisions are made at 3 Closed Loops—a tailored and personalized one for patients, and evidence-based one for clinicians by incorporating guidelines and protocols, and finally a futuristic one by collecting data for population health. The disclosed CDSS is built upon a Knowledge-Based Machine Learning algorithm and the hypotheses are generated in a supervised mode. The disclosed system utilizes clinical features patients report to classify them to particular clinical entities for 'pattern recognition' and matching rather than a conventional 'inclusion/exclusion criteria or rate estimation'. The approach adds value in delivering precision medicine in a simple, inexpensive, and in a reproducible manner which will set a new standard in healthcare delivery.

Successful implementation of the machine learning model of the disclosed CDSS will foster the transformation of the current healthcare system into a 'learning health system' that generates and applies evidence naturally for the effects to transfer for population health. A population health-based view grounded in the principle of getting the right information to the right member of the healthcare team—including the patient—at the right time during the workflow for optimizing the decision-making process is a need for this time.

The disclosed system may allow learning from every patient that navigates through the healthcare system. The objective is to turn an individual's data into useful information that can guide intelligent action and aggregate this patient-level information to show quantifiable results within the clinical microsystem, the healthcare macrosystem, and the community. A major step to this would be more standardized, systematic, and patient-centered data collection which is stored in a central registry for future research and analysis. The central registry can act as a research database for learning how to reliably produce better health outcomes, higher quality, and better value. This will further enable more efficient delivery of precision medicine by making better-informed decisions.

The disclosed system may be used by insurance companies to create grading for clinicians who are providing quality care through lesser utilization of resources meanwhile, delivering high patient satisfaction. It can further yield to have a merit-based reimbursement model for providing value-based care rather than having procedure-based incentives. The screening tool can also be tailored for patients to decide upon the appropriateness or urgency in seeking care from the emergency department to filter the influx.

The disclosed system will be equipped to integrate deep learning features as it gains more data and knowledge to make the system superior to human intelligence and judgment. Care is coordinated around populations, and the care delivered is right for the individual through the systematic use of evidence. Each individual is a data point in a population database. Providers are taught to practice in multidisciplinary, high-performance teams, using simulation to perfect their skills and outcomes to guide course corrections.

Further, the disclosed system may become the healthcare standard in musculoskeletal care. It may even automate Spine care with future integration of 'treatment-based classification'. Research is required to verify the feasibility to apply the same approach to other peripheral joints and also to other fields of medicine.

Further, the disclosed CDSS incorporates machine learning algorithms in conjunction with the human brain to identify intricate and potentially undetected patterns creating predictive models easily adaptable to the clinical flow. Once the model is tested and proved viable, CDSS can serve as a legitimate clinical decision-making tool in spine care. Serving as a reliable source CDSS will improve clinician performance and promote appropriate, efficient care in this era of person-centered, value-based healthcare delivery.

In the face of technological upsurge, the medical system is more skewed to investigation-based treatment than patient-centered care to 'identify and isolate' the tissue or structure at fault in each episode. Health professionals rely too much on investigative procedures to 'label' a person and or to rationalize patients' complaints. This low-value care is non-discriminate between different payer types and has become a 'cultural norm' among providers and patients in US healthcare [6].

High-quality history taking can be considered an art to be mastered. Unfortunately, a patient's history is subject to the healthcare provider's skepticism, interpretation of their biomedical knowledge, bias by experience, and skill to tease out the 'facts'. Stereotyping and biases by itself will lead to misdiagnosis, inappropriate plan of care, and overutilization of healthcare resources. It is essential to understand each patient's unique story and disease process to document and deliver the most appropriate effective care. Moreover, the law enforces the same.

The marked proliferation of innovative technologies has resulted in an exponential increase in the cost of healthcare (with no improvement in health outcomes). It is fair to say that the additional information gained has no benefit to the patient. With the emergence of clinical subspecialties and super specialties, the disease boundaries have changed, precise and targeted care has led to redundancy, more waiting period, overdiagnosis, and overtreatment. A majority of people do not require medical treatment rather they benefit from education and reassurance. Oftentimes the fear of uncertainties drives patients to seek medical care, they are misdiagnosed or over diagnosed and treated symptomatically leading to chronic stages and dependency. A huge erosion in clinical quality has happened when the system shifted gears to image-focused healthcare delivery rather than understanding the individual patients and their challenges. Spine care is consistently maintaining a high profile clinical entity in the healthcare industry, not only by its prevalence but because of its multifaceted impact and associated cost.

Further, the disclosed CDSS comprises skillfully planned questions incorporating the sophistication of information technology with evidence, experience, and expertise in spine care to create a virtual interaction with their prospective clinician. Further, the virtual interaction may be different from true interaction. In an instance, the virtual interaction may include chatting to a chatbot with a profile picture of the clinician that may indirectly provide a feel of chatting to the user. The goal is to arrive at a suggestion of best practice while eliminating the missteps that may be caused by personal idiosyncrasies.

Further, the disclosed CDSS may triage spine related pathologies by identifying patterns, following algorithmic approaches to develop and define care pathways, to predict risk, and even to make accurate diagnoses. The disclosed CDSS classifies spine pathologies into various subgroups along with conventional pathoanatomical models whenever it's applicable. Spine pathologies have a significant biopsychosocial aspect that affects the recovery and prognosis causing the reliance on the selected pathoanatomical model alone to fail over and over. The supervised machine learning model recognizes patterns just as a clinician makes decisions—and it relearns, refining its accuracy over time as it ingests greater amounts of information.

The disclosed CDSS may be a 'gatekeeper' in directing urgency and preventing overutilization of resources. The disclosed CDSS identifies co-morbidities, detects sinister pathologies through guideline-based screening, highlights risk factors and or severity, and gathers information on prior treatments and their effectiveness. The disclosed CDSS is ideal to triage spinal pathology, facilitate early identification, decrease overutilization of resources, and prevent chronic pain crises thereby promoting health while adding value in healthcare delivery.

Patient-centric Data Entry/Assimilation—The disclosed CDSS is built upon a systematically organized, unbiased, uninterrupted, detailed first-hand report of patient history 'deliberately' untapped by the current system and is embedded 'within-the-loop' to enhance the patient experience. The disclosed CDSS is designed to capture high-quality, patient-centric data in a standardized way that empowers clinical reasoning to deliver optimal care. In an instance, the disclosed CDSS may include at least 20 spines related Clinical Prediction Rules and or Guideline based treatment protocols.

Gathering patient-specific information will sharpen the clinical reasoning, more precisely target further examination—leading to informed decision making and patient-specific treatment plan. The detailed patient-centric documentation of 'refined data' further facilitates accurate analysis and prediction. Machine learning will reinvent clinicians' roles giving them more time to focus on value-based care. Further, Therapha™'s summary would be provided with details helpful for patients to understand the thresholds used to trigger alert, clear instructions for patients on the next step in the process, and further grade that urgency. The incorporation of clinical prediction rules and guideline-based treatments improves the tool's sensitivity and specificity. Therapha™'s alert system activated with a combination of signs or symptoms rather than a standalone 'redflag' feature makes it more reliable.

The disclosed CDSS may facilitate the optimal utilization of resources. Incorporation of various risk predictors facilitates direct specialist care or referral remotely, more personalized diagnosis and treatment, decreasing overutilization of resources. The data collected may be very detailed, documented appropriately for clinical practice and research purposes without the clinician investing his skilled time for clerical work. Clinicians are overburdened by their dual-role of the dutiful obligation of record entry to EHR (for clinical, research, and or legal purposes) obstructing their professional responsibility to deliver the best possible care for the well-being of patients.

The disclosed CDSS may include comprehensive screening software. The disclosed CDSS is transparent as the logic is easily understood and the concepts can be easily explained. The disclosed CDSS may generate hypothetical diagnoses that are parallel to the generation of diagnoses by the conventional clinician's thought process and are as easily presented and understood. The 'Patient-centered and Shared decision making' nature, will make patients more accountable to their healthcare delivery by having better understanding and adherence to treatment and self-management strategies.

The disclosed CDSS aids clinicians in acquiring a comprehensive understanding of the patient and his story. The provision of a structured patients' version beforehand and recounting it to them helps in building rapport establishing trust and respect in the initial encounter itself.

The disclosed CDSS is cost-effective for health systems as it is not disruptive to the current workflow, there is little or no learning curve. It will assist the clinician with decision making, save skilled time now spent on routine data entry, aid in early detection identifying targeted treatments, identify high-risk patients and redirect them for multidisciplinary care, and decrease overutilization of resources.

A study associated with the disclosed system is designed to use a logistic regression method to test the prediction using the disclosed CDSS. The logistic regression method is justified and appropriate given the nature of the dependent variables (diagnoses) and the independent variables (signs and symptoms) that have been clinically deemed to be predictors of such diagnoses. The study plan will be analyzing the predictability and specificity of the disclosed CDSS for generating clinical hypotheses, sensitivity in identifying sinister pathologies, and the significance of the role of each independent variable. With a representative sample and large enough sample size, the study will be efficient and adequately powered to answer the research question(s), test the proposed hypothesis/hypotheses, and provide interpretable results.

The multifaceted nature of the spine provides flexibility to research different levels—depending on the regions like cervical, thoracic, lumbar, and pelvis. Studies can also focus on its effectiveness when conducted by a patient independently or in conjunction with the clinician. The disclosed CDSS may also be evaluated for its efficacy in identifying sinister pathologies to use as a triaging modality which is ideal for telemedicine. The overall outcome can be combined or separately tested to utilize the same as a self-initiated triaging for any spine-related pathologies.

The disclosed CDSS would be a perfect launching pad to integrate updated clinical practice guidelines into everyday clinical practice. This 'conspicuous way' of assimilation without any change in the current workflow will be more effective in changing clinician behavior than the traditional passive educational approach and can drastically narrow the knowledge-to-practice gap.

The intersection of science, technology, medicine, and brilliant minds that have and or can integrate all or most of them are the ones who keep the medical field improving.

The knowledge repository must be kept abreast of new knowledge acquisition and include a filtering system developed to prevent the potentially deleterious impact of poor data quality and incorrect content.

Even though much research has established the utility of 'Medical History Taking' towards clinical diagnosis generation, the disclosed system is innovative as it is exploiting the unseen potential of information technology—machine learning in particular.

Most innovations without clinician participation fail prematurely or result in products, tools, and services that are suboptimal because they were not directly designed into the clinical workflow but rather force-fit into the process. Anything disruptive in nature to the clinical workflow will face resistance and will die in the cradle. The disclosed CDSS differs significantly from the old one-doctor, one-patient, one-exam-room, paper-record model. Clinical decisions are made at 3 Closed Loops—a tailored and personalized one for patients, and evidence-based one for clinicians, and finally a futuristic one for population health. The disclosed CDSS is designed with a novel patient-centric, data-rich, feed-forward information environment with real-time actionable feedback in the form of decision making which is not disruptive to the clinical workflow yet will be disruptive for the future spine care delivery.

Further, the disclosed system may include Therapha™. Further, the Therapha™ may be a registered Trademark under the company name AIINPT, Inc. By functionality. Therapha™ can be considered as a patient-self-administered (or in conjunction with the clinician), Comprehensive Screening Software (or software), with hardware components, designed to identify patients with high risk or who require medical attention. The software is not designed to replace health care experts but to enhance the treatment outcome cost-effectively and scientifically by making them better informed. In the terminological category, Therapha™ is a Clinical Decision Support System (CDSS) utilizing Machine Learning and Computer Vision in improving clinical reasoning and productivity. Therapha™ can be better expressed as and by the concept of "human-assisted computer diagnosis".

Further, the Therapha™ may include a machine learning-based clinical utility algorithm for clinical decision making. Further, the Therapha™ may aid in decision making for Spine related care (for now, can develop for other joints in the future) and also, the same principle can be applied to other outpatient medical conditions as well. Utilizing the Machine Learning Model, the Therapha™ predicts a provisional diagnosis for spine-related pathologies through a series of questions to generate an algorithm. The questions can be answered either through a web-based patient-self-administered form or a combination of interaction between the patient and the clinician. The former saves clinicians valuable one-on-one time for more informed decision making and to direct examination more accurately. The beauty is that it has high sensitivity to detect Sinister pathologies like and not limited to Cancer, Vertebral/Rib Fracture, Spinal Infection, Cauda Equina Syndrome, Ankylosing Spondylitis/Autoimmune Diseases (using Berlin Criteria), Deep Vein Thrombosis, Pulmonary Embolism (using both Wells and Geneva Score), Screening for Depression (using PHQ-2), Need for C-spine X-ray (through Canadian Cervical Spine Rules), etc.

Therapha™'s patient-facing triaging tool ruling out any medical considerations/emergencies and ruling in ideal candidates for conservative and or for rehabilitative care even before a formal visit with the clinician by utilizing the Clinical Decision Support System (CDSS). The machine learning model associated with the Therapha™ may predict the Hypothetical Diagnosis/Classification/Traffic Light Model to alert the clinician on how safely they can proceed even before they see the patient in person or while they are doing the questionnaire along with the patient. This makes Therapha™ a handy 'risk predictor' at the point of contact. The biggest take away is not with generating the hypothesis but decoding of all those entries into a Clinical Note format for the ease of documentation. Studies proving the system works will lead to early detection and more focused treatment options, a significant reduction in imaging cost and overutilization of medical resources, improved productivity and patient satisfaction, the avoidance of unnecessary drug usage and addiction, and more importantly patient-centered care.

Further, patients are provided with a series of questions to generate an algorithm. These questions can be answered either through a web-based patient-self-administered form or a combination of interaction between the patient and the clinician during the patient's in-person visit. Patients are provided with a wide variety of meticulously constructed options to choose (to prevent noise in data analysis) or if necessary free text for responses in the designated column. Further, the disclosed system is equipped with transforming free-text documents which are represented by set words (called features) in a more computationally friendly format to a vector of numerical descriptors. The Therapha™ is intended to help patients and their clinicians make more informed decisions and the same will be auto-posted or imported to their Clinical Notes for the ease of documentation for the clinician to avoid redundancy and to save valuable skilled time. Therapha™'s implementation and acceptance will lead to better outcomes for patients, a more enjoyable culture, fewer healthcare disparities, better utilization of resources, and an enhanced customer experience to patients.

The disclosed system may be designed to create a 'digital twin' of the patient by transforming the patient-specific data into numerical values for computational efficiency in the preprocessing stage. Those values derived are vigorously analyzed and filtered to establish a clinical correlation between any unique symptoms or groups of symptoms (syndrome) for a particular diagnosis or other similar diagnoses. Condition-specific data is fed into the 'Knowledge Repository' in the system under different categories, like age-specific, symptoms unique to certain conditions, condition-specific symptom patterns, history of present illness, various other factors like past medical information and previous similar history along with any treatment and their effectiveness are also taken into consideration while concluding the filtering process. One of the unique features incorporated in the presence of a very well diced body diagram which follows a dermatomal pattern behind the screen, this will help in prediction by matching the respective pain map in the knowledge repository. The data extracted from patients are compared with the ones in the knowledge repository. The knowledge repository is modeled as a set of 'if-then rules' and certainty factors to rule in and out a clinical hypothesis to generate a probability of the same.

Therapha™ may use Pathoanatomical Diagnosis for predictive hypothesis but understanding the complexities involved with the tissue-specific diagnosis in spine care, it has successfully incorporated various other classification systems like ICD-10, McKenzie Method of Mechanical Diagnosis and Therapy, Impairment-Based International Classification of Functioning, Disability, and Health (ICF), and American Physical Therapy Association Guideline based Classification to predict/hypothesize a clinical condition. This kind of integration of a different classification system to label a clinical diagnosis is also unique and will encourage uniformity in the medical practice irrespective of the differences in a school of thought. This will ultimately lead to providing the necessary care to the sufferer rather than the disparity in schools of thoughts or other ideological differences.

A set of differential diagnosis or a provisional diagnosis is disclosed based on the Smartform (data) the patient completed and is compared against the 'keywords' in the knowledge repository. The disclosed hypothesis is not merely based on medical taxonomy alone, but also by another system like an evidence-based classification system that understands and follows the path of clinical reasoning and true experience a clinician employs while interacting with their patients during an evaluation [3]. This platform and feature significantly improve human decisions by expediting information retrieval, identifying unique patient needs, triaging care, and matching patients to the most appropriate resources and treatment [4].

The following are the steps involved in the utility of features associated with Therapha™.

1. Extracting Patient Data through a series of questions.
2. Analysis of the data acquired using the Statistical tool (called Discriminant Analysis).
3. Matching the result of the (Discriminant) Analytic data against what is in Knowledge Repository to a specific Clinical condition or group of similar conditions.
4. Identify Risk Factors involved by Ruling In and Out Yellow and Red Flags.
5. Generate differential diagnosis to provide a Provisional diagnosis depending upon the probability prediction
6. Recommend a treatment-based classification Thus the clinical hypothesis is generated based on a combination of current evidence-based research and in the light of expert knowledge. The results obtained will be verified during the in-person clinical examination to abort or to accept the hypothesis (Supervised algorithm to train the Machine Learning process). This process will further refine the system to improve its prediction accuracy.

Further, the disclosed system may include a component-based tracking/visual tracking of human joints for measuring joint range of motion and analysis and or detecting deviation from the standard posture.

Further, the disclosed system may include ProGonio that may be powered by Artificial Intelligence (AI) utilizing Machine Learning (ML) and Computer Vision in creating a model which will be the Gold Standard in the musculoskeletal industry for joint-related pathologies. The ProGonio may be configured for accurately measuring the human joint range of motion. Its accuracy and consistency in measurement along with its decreased variability in reading by the same clinician and between different clinicians fortify the statement. Additionally, a unique feature is its ease of use. This not only saves time during measurement but increases reproducibility and allows for measurements to be used in Electronic Medical Records (EMR).

In the medical field, professionals use the Goniometer regularly to assess the progress or regress in their patients. Irrespective of the fact that it is difficult to position and maintain arms of the Goniometer along with the reference landmark and the axis of rotation is an assumption, there is no effective replacement for this age-old instrument. In addition to strength measurements, a joint range of motion is the only objective finding demonstrating the efficacy of care.

Further, simplicity to use and reproducibility associated with The ProGonio irrespective of the clinical experience or skill of the clinician makes a potential product of choice for all. The inbuilt tutorials and reference guides are meticulously designed to produce low error rates aiding any clinician to be a Pro. Powered by AI, utilizing Computer Vision, ProGonio is the only Mobile Application designed to measure real-time individual human motions in a matter of seconds.

The ProGonio may be used remotely for Telehealth. The ProGonio may not require sophisticated equipment, other than a smartphone with ProGonio application. The ProGonio may be configured for real-time reading and measurement. Results associated with The ProGonio may be easily reproducible and consistent. The ProGonio may require minimal to no skill or training required. From start to end, the process is done wirelessly.

Further, the disclosed system may be integrated into a mobile application to be easily accessible. Further, The ProGonio may be configured for real-time pose estimation, vision-based human body motion. Further, The ProGonio may be associated with computer vision non-contact method and no additional wearing identification devices may be worn.

Using Component-Based tracking/Visual Tracking of human joints incorporated into Machine learning is the key process involved in the functioning of ProGonio. The ProGonio may implement image processing and object detection through Visual Tracking/Person Tracking, using the camera in a smartphone. The trained data models will be used to identify the reference points of joints from the patient and thereby allowing the system to calculate the angles between the selected joints. A mobile application will be used to capture the patient's selected joint movements and the respective angles between them. Initially, the mobile application may provide a whole-body layout from which a specific joint can be selected. Once the required joint is selected, details corresponding to that joint will be displayed. On confirming the joint to be captured, a camera layout with a reference position for the angle measurement of the selected joint will be shown. The patient can align their body parts with reference to the layout provided for the same. Upon aligning the body parts using the camera in real-time, captured data may be provided to the trained data model, which will then process the captured data to predict the reference points and calculate the angle between them in real-time. Upon prediction of the reference points, the trained data model may start a real-time measurement that may be saved. The joint measurements may be taken in one after the other manner and each measurement may be saved for later retrieval. The final measurements may be delivered as a report that may be readily entered or auto-posted to the EHR system.

Further, the disclosed system may include PosturePro (an exemplary embodiment of the CDSS disclosed herein). By utilizing the same model used in the ProGonio, any postural deviation associated with the patient may be analyzed and identified if the patient exhibits, especially with certain neurological pathologies like Parkinson's Disease or people who have suffered a stroke. The same feature can be used for Scoliosis screening and prognosis purposes in schools and during recruitment procedures in the military etc. This functionality can be utilized for prognostic purposes as well as periodic reviews or screenings.

After successful processing of data, a report will be generated and displayed to the user, who can then include all other physical findings into the evaluation summary to establish a clinical correlation that will be instrumental in establishing the final diagnosis, leaving the clinician to make the final call and thereby truly acting as a support system. These features can be successfully incorporated into any telehealth platforms separately or as a bundle to make the evaluations or subsequent consultations standardized. Because no other parallel nonwearable technologies which can remotely access patients exist these features are unique.

A unique feature in the industry, the Therapha™ offers is a 'Documentation-Based Clinical Decision Support System' designed to gather patient-specific information in a very organized manner via Smartforms. They are designed to develop and establish an engaging communication system even before they meet in person for their initial evaluation. It enables the clinician to obtain patient-specific data accurately on time to enhance patient care. Further, the system avoids redundancy and promotes the optimal utilization of both patients and the clinician time [2]. Data gathered from the Smartform are automated into a medical note format for the clinician to save time from documentation, to have a place where all the clinically relevant individual facts about the patient are organized for clinical reasoning and the decision-making process. This information can be utilized to narrow down clinical examination which along with the information either filled out by the patient self-administered and later verified by clinicians or along with the clinician during the patient's in-person visit will be instrumental in tailoring the most efficient and effective diagnosis and treatment.

The incorporation of features associated with the disclosed system into current practice will pave the way for optimal use of time and enhance patient-clinician relationships, further hastening recovery by incorporating the latest advancement in technology. The features associated with the disclosed system will be able to run as an application on a handheld device like a smartphone or tablet will make this accessible and popular. It also addresses the dire need to make effective clinical judgments substantiated by clinical reasoning and is evidence-based. This is the ultimate use of technology to bring a dramatic change in our ailing healthcare industry effectively, efficiently, and sensitively.

TheraScope may establish a clinical correlation between the physical impairments in the musculoskeletal system which is collected through subjective complaints and linking that data to the most applicable clinical entity or other similar conditions. TheraScope enables the clinicians to filter down to the differential diagnosis even before they initialize the examination process. Plans include establishing a provisional diagnosis for the virtual twin to aid the clinician in clinical reasoning and justification in treatment choice. Effective treatment comes from the efficient analysis of data gathered and interpretation of clinical findings in coming to a treatment conclusion which often comes from clinical experience. The whole platform is designed to initialize care at the convenience of the patient's home.

Further, the disclosed system may include a non-invasive fall detection system based on the center of gravity and base of support of the human body. During day to day life, falls can be dangerous and can lead to death or disabilities. Different technologies have been developed and used to identify a fall and provide warnings and emergency messages as explained in [1]. Wearable devices are popular yet not always dependable in terms of durability and accuracy. For the geriatric population, wearing a gadget all the time is infuriating and a non-invasive approach is more favorable. The disclosed system functions based on the concept that the probability of a fall is directly correlated to a person's body posture. A video camera is used to monitor a person's body posture without requiring to have any wearable devices. This video feed is then used in conjunction with a specially designed, novel software to analyze the members of the body and form a prediction of the probability of a fall. The stability and the chance of fall of a human body can be explained as a function of the distance between the center of gravity (COG) and the base of support (BOS) point. The BOS point typically lies anterior to the second sacral vertebra and for the disclosed system, it will be taken as such.

The center of gravity can be calculated using the following system of equations where x, y, z represents the known coordinates of the center of gravity of each member of the body. m represents the mass of each of these members which are calculated as a percentage of the total body mass. The selected members are described in more detail below.

$$COGx = x1m1 + x2m2 + x3m3 + \ldots m1 + m2 + m3 + \ldots \quad \text{(Eq. 1)}$$

$$COGy = y1m1 + y2m2 + y3m3 + \ldots m1 + m2 + m3 + \ldots \quad \text{(Eq. 2)}$$

$$COGz = z1m1 + z2m2 + z3m3 + \ldots m1 + m2 + m3 + \ldots \quad \text{(Eq. 3)}$$

Landmark points will be taken from different members of the body such as shoulders, elbow, wrist, finger, hip, knee, ankle-foot, toes, cervical spine, and thoracic spine. For the system to accurately track these points, it will utilize Computer Vision and Machine Learning. The software will track the needed landmarks on the incoming video feed to generate the coordinates needed for the COG calculations.

Once the COG has been calculated, the distance between the BOS and the COG can be determined. Thus, from this value, the probability of a fall can be predicted.

Further, a person's stability can be computed from the COG and BOS. More specifically, when the line of gravity (a plumb line drawn from the COG) is in line with the BOS, the person is considered to be in a stable condition. When the line of gravity is no longer aligned with the BOS, the person is considered to be unstable, meaning the chances of a fall are high. As the distance between the line of gravity and the BOS increase, the probability of a fall will also increase.

Finally, the system will produce suggested movements or alterations in a posture to increase the person's stability. By applying Newton's First Law of Motion through the equilibrium equation (Eq. 4) a resultant force can be computed. This resultant force signifies the movement that is necessary to align the COG with the BOS. The software will then translate this into adjustments that are needed to achieve stability.

$$F = 0 \quad \text{(Eq. 4)}$$

Further, the disclosed system may replace a primitive human joint range of motion measuring tool—the Goniometer. Embracing recent advancements in technology and integrating years of clinical experience paved the way for a revolutionary innovation—the ProGonio. Further, the ProGonio may invariably change medical practice, particularly in the area of musculoskeletal care across the globe.

Further, the ProGonio may be powered by Artificial Intelligence (AI) utilizing Machine Learning (ML) and Computer Vision. Further, the ProGonio may be the gold standard in the musculoskeletal industry for joint-related pathologies. Further, accuracy and consistency associated with the ProGonio in measurement along with its decreased variability in reading by the same clinician and between different clinicians fortify the statement. Additionally, a unique feature of the ProGonio may include ease of use. This not only saves time during measurement but increases reproducibility and allows for measurements to be used in Electronic Medical Records (EMR).

Applying the most advanced technology (AI) and confining the product into, for example, a mobile application (App) makes the ProGonio available to everyone in the medical field, regardless of the title they hold. From medical students to Orthopedic Surgeons, the ProGonio may be the tool for all.

In the medical field, professionals use the Goniometer regularly to assess the progress or regress in their patients. Irrespective of the fact that it is difficult to position and maintain arms of the goniometer along with the reference landmark and the axis of rotation is an assumption, there is no effective replacement for the goniometer. In addition to strength measurements, a joint range of motion is the only objective finding demonstrating the efficacy of care. Between patients who are extremely eager to know what is going wrong, or those who are anxious to self-diagnose through online research, and clinicians working to acquire the latest advancements in healthcare, ProGonio is an answer. Further, simplicity of use and reproducibility of the ProGonio irrespective of the clinical experience or skill of the clinician makes it a potential product of choice for all. The inbuilt tutorials and reference guides are meticulously designed to produce low error rates aiding any clinician to be a Pro.

Further, the disclosed system may transform the existing electronic medical records and patient engagement in the global healthcare industry. Further, the ProGonio, replacing the traditional joint range of motion measuring instrument goniometer, maybe a great addition. Further, software codes (or code) of a software application associated with the ProGonio may be utilized for more sophisticated assessments as gait evaluations, fall risk screening, posture analysis—screening for scoliosis in schools to more aggressive screening procedures as in Military recruitments and to optimize performance in sports and athletic fields. Further, the codes may be converted for various other applications, from highly sophisticated high-end security cameras to make the public as the end-user through a simple weight and waist watcher app. Fundamentally, the utility of the code that may work on a smartphone is multifaceted.

Further, the goniometer may include a diagnostic measuring instrument. Further, the goniometer may be used in the medical field by the clinician, surgeons, rehabilitation doctors, etc. to measure a patient's progress. Further, the goniometer may be difficult to use due to the alignment that is needed, and it is impossible to measure the range of motion remotely, making ProGonio the only objective measurement that can be obtained in a tele healthcare delivery model. Use of the goniometer leads to a time-consuming, uncomfortable process for patients and practitioners. Further, the goniometer may require the practitioner to purchase additional equipment (the goniometer). Further, the reliability of the goniometer may not be good. Further, existing applications associated with the goniometer may be configured for performing accelerometer-based analysis. Further, the existing applications associated with the goniometer may use the accelerometer in the device to track the range of motion. This method is extremely prone to inaccuracies as any shifting in the device will offset the calibration. Further, certain movements of the body may not be able to be tracked as there is no change in slope. Further, existing digital goniometers may require the practitioner to purchase a separate device. Further, the digital goniometer may be time-consuming and uncomfortable for the practitioner. Further, the digital goniometer may require the practitioner to press a button associated with the digital goniometer to enter measurement mode. Further, the practitioner may align the digital goniometer with a first limb and then press the button again to start measurement. Further, the practitioner may align the digital goniometer to a second limb and press the button end the measurement. Further, a measured angle may be calculated and shown on a display associated with the digital goniometer. Further, the practitioner may press the button again to view the measured angle along with the last four measurements measured by the digital goniometer.

Further, the ProGonio may include a simple, easy to use application for the clinician to examine the patient's range of motion. Further, the physical therapist may select a body part (or joint) that may be measured. Further, the physical therapist may point the camera at the body part that may be selected. Further, the application may show the identification of the joint and may display measurement for the joint. Further, the ProGonio may use computer vision to track joints and compute an angle measurement for a range of motion computation. Once the user selects a joint to measure, the camera may launch in the application. Further, a script associated with the ProGonio may run to identify reference points used for measuring the angles. Further, the reference points corresponding to the joint (that may be selected) may appear on the screen associated with the smartphone. Once the reference points are identified, a measurement is taken and reported back to the user. Further, the script may be configured for real-time pose analysis using the webcam of the computer. Further, an algorithm associated with the script may be configured for identifying the reference points on the body and track movement of the reference points. Further, vector lines (or vectors) may be placed between corresponding reference points to better display the pose tracking. Further, the vectors may be used for measuring angles associated with the body. Further, the script may be configured for computing the angles and display to the user. Further, the application associated with the ProGonio may include a simple easy to navigate user interface.

Further, posture is an attitude assumed by the body, either with support during muscular inactivity or using the coordinated action of many muscles working to maintain stability. Further, the posture may be defined as the relative arrangement of different parts of the body with a line of gravity. Further, a detailed evaluation of posture is a prerequisite in determining the correct management and progress. Further, the evaluation may be performed to see if there are any muscular imbalances or undue strain in the joints which could cause or are causing pain and discomfort. Further, existing methods for posture analysis may result in many inaccuracies. Further, diagnosis associated with the posture analysis may be inconsistent between practitioners as well as between examinations. Further, the diagnosis may not quantifiable and thus cannot be used for measuring progress. Further, existing methods for posture analysis may be time-consuming and inefficient for practitioners. Further, mechanical methods associated with posture analysis may include a visual observation method and plumbline and grid method. Further, the clinicians may visually inspect patients to determine possible deformities in the patient's posture. Further, diagnosis associated with the visual observation method may be subjected to the clinician's judgment leading to extreme variability. Further, quantitative data associated with the posture analysis cannot be collected by the visual observation method. Thus minor postural alterations may not be detected. Further, posture may be evaluated in accordance with the accepted posture guidelines of the ideal plumb line alignment. Further, the plumbline and grid method may not produce quantifiable or repeatable data. Further, the plumbline and grid method may be physically intensive for clinicians and produces sub-standard results. Thus, the plumbline and grid method are rarely used.

Further, existing digital methods associated with the posture analysis may include a photographic method, a radiographic method, and a photogrammetric method. The photographs of the patients may be compared to an accepted "Good Posture" image. Further, in the radiographic method, the posture of the patient may be evaluated from X-ray images of the patient. Further, the results of the radiographic method may be considered gold standard measurements due to the accuracy and precision of the images. Further, the cost and harmful effects of radiation discourage the use of the radiographic method. Further, in the photogrammetric method, the posture of the patient may be evaluated from the image of the patient that is analyzed through computer software. Further, the computer software analyzes the image to calculate deformities from an ideal posture. Further, the photogrammetric method produces accurate, quantifiable results, but requires additional equipment and processing for the clinician.

Further, the reference points may be compared to an ideal model for postural assessment. Further, deviations associated with the posture of the user may be quantified and reported to the user. Further, the posture may be assessed in both an upright and seated position. Further, the existing application may not use real-time analysis limiting the diagnosis ability of the clinician.

Further, the disclosed system may include a simple, easy-to-use application for the clinicians to assess the posture of patients and diagnosis any structural deformities. Further, posture analysis may be performed while the patients are sitting or standing. Further, the application associated with the disclosed system may be used in schools for scoliosis screening, military for work re-entry.

Further, the disclosed system may be configured for creating a real-time computer vision-based application that tracks the movement of the human body and determines deviations in the posture. Further, a script may be run to analyze the real-time image to identify the joints and track them relative to each other. The joints may be compared to designated values to quantify the patient's posture. Further, the device used may be held level to properly analyze the patient. The device accelerometer may be used for this purpose.

Further, the script associated with the disclosed system may be used in conjunction with additional code to perform posture analysis. Further, the script may be run to identify the reference points on the patient. Further, the script may be configured for confirming the device is level (using the device's accelerometer). Further, the script may be configured for transmitting a form of feedback to the user letting them know when the device is in the correct position. Further, the script may be configured for comparing the patient's posture to a baseline posture. For instance, if one shoulder of the patient is lower than the other, the connecting line will be sloped rather than level. The slope signifies the deviation in the patient's posture. Further, the script may be configured for reporting a discrepancy upon identification of the discrepancy.

Further, human intuitive judgment and decision making are subjective skills and highly varied between individuals and can be far from optimal, and it deteriorates even further with complexity and stress. In any situation, especially in healthcare, the quality of decisions is important; therefore, aiding the deficiencies of human judgment and decision making has been a major focus of science throughout history. Further, Clinical Decision Support Systems can aid human cognitive deficiencies by integrating various sources of information, providing intelligent access to relevant knowledge, and aiding the process of structuring decisions [13].

Further, the CDSS may include an electronic or non-electronic active knowledge system specifically designed to aid in clinical decision-making, in which parameters of individual patient health can be used to intelligently filter and generate patient-specific evaluations and assessments which serve as recommendations to clinicians during treatment, thereby enhancing patient care." [13]

Further, the CDSS is an information technology tool that, depending on the patient's input data, can give assessments, prognosis, and medical recommendations based on the nature of the medical condition. Further, the CDSS may galvanize the field of health care [13]. Traditionally healthcare delivery is solely based on medical knowledge and experience. Among numerous limitations of these systems, a few which require attention are disparity in quality of care delivered across the nation and identification of hidden patterns which leads to better clinical management and patients' outcomes [15]. Implementation of proven CDSS may help in providing standardized care across the spectrum.

Interpreting clinical data to classify patients on time has impacts on costs, productivity, efficiency and is more importantly vital in providing optimal care [15]. There is a huge need for a CDSS in the musculoskeletal field designed with intelligent techniques that can overcome all presumed challenges, and to integrate at the point of care which falls 'within-the-loop' would be disruptive in the current healthcare industry.

Unlike other existing CDSS, Therapha™'s internal process is transparent and may be explained in a humanly comprehensible manner, eliminating the 'Black box' effect. Moreover, interpretability of the Therapha™ ensures accountability, fidelity, algorithmic fairness (fairness property ensures that the model should not favor certain cases over others, such discrimination mainly arises due to biases in the training data), robustness, and generalization to the given adult population. This invariably helps in the smooth deployment and functionality of the tool in realistic settings [16].

Further, the questionnaires are meticulously crafted using languages that are comprehensible for an 8th grader to capture fine-grained symptoms without ambiguity. Oftentimes, inputs are extremely noisy either because there are too many questions unanswered, misunderstood because the lack of clarity or the presence of other comorbidities leads to misrepresentation of clinical entities corrupting the algorithm and prediction. Therapha™ is created with this consciousness and all efforts are made to ensure the inputs are specific to their current episode or condition of interest rather than a generalized list of concerns.

Understanding the complexities involved with the tissue-specific diagnosis in spine care, Therapha™ has utilized a classification system to formulate the output—differential diagnosis nomenclature and has successfully incorporated 4 different popular classifications—ICD-10, McKenzie Method of Mechanical Diagnosis and Therapy, Impairment-Based International Classification of Functioning, Disability, and Health (ICF), and American Physical Therapy Association Guideline Based Classification in labeling the underlying spinal pathology. This will pave the way for unified agreement across the board and further leads to targeted care on time.

Further, input data associated with the existing CDSS may be obtained from electronic health records (EHRs). Further, the Therapha™'s input (History, symptoms, and signs) may include first-hand information by patients themselves. Through self-administered questionnaires or in conjunction with their clinicians, Therapha™'s input is free of bias and is complete with deliverables at the point of initial contact without disrupting the clinical workflow. Problems with the input data coming from EHR's may include a heterogeneous structure of EHR [14]. Further, diagnosis labels on EHR data are often based on ICD codes which are primarily billing codes and are not a true representation of ground truth disease code [14]. Further, history and documentation in EHR are clinician's witness reports of facts and are often biased. Furthermore, the integration of Therapha™ cleans up messy and erroneous medical documentation into more systematic electronic records where even patients' self-reported symptoms can be stored into codable data. This will further facilitate uniformity in the field leading to more accurate research, education, and creation of a central data bank.

Further, an output associated with the Therapha™ is generated in a manner that is useful to the patient, through a clinical diagnosis or differential diagnosis which is not shared with them. As warranted, Therapha™'s summary would provide details helpful for patients to understand the thresholds used to trigger an alert, clear instructions for patients on the next step in the process, and further grade its urgency. The incorporation of clinical prediction rules and guideline-based treatments improves the tool's sensitivity and specificity. Therapha™'s alert system activated with a combination of signs or symptoms rather than a standalone 'red flag' feature makes it more reliable. The triaging tool along with the pertinent clinical summary is informative and reassuring for them. Further, Therapha™ is ideal for online telehealth settings where the patient uses the platform with no lab results or has a physical exam done [14].

Further, Therapha™ may include a CDSS associated with the musculoskeletal field more specifically for spine-related pathologies. Further, Therapha™ integration may not be disruptive to the clinical workflow as the deliverables are at the initial point of contact. Since the Therapha™ requires no training and is not disrupting the current workflow, there would be greater receptivity from healthcare providers and greater success in its implementation. With the incorporation of TheraScope, ProGonio, and PosturePro using unbiased first-hand information, spine triaging will have the potential to revolutionize musculoskeletal care. Further, the incorporation of Evidence-based Clinical prediction Rules and Guidelines ensures consistency and best care for all. The outcome primarily focuses on improving the diagnostic accuracy, enhancing treatments, and reduction in the variation on medical decisions involved [15].

Referring now to figures, FIG. 1 is an illustration of an online platform 100 consistent with various embodiments of the present disclosure. By way of non-limiting example, the online platform 100 to facilitate predicting a diagnosis of musculoskeletal pathologies may be hosted on a centralized server 102, such as, for example, a cloud computing service. The centralized server 102 may communicate with other network entities, such as, for example, a mobile device 106 (such as a smartphone, a laptop, a tablet computer, etc.), other electronic devices 110 (such as desktop computers, server computers, etc.), databases 114, and sensors 116 over a communication network 104, such as, but not limited to, the Internet. Further, users of the online platform 100 may include relevant parties such as, but not limited to, end-users, administrators, service providers, service consumers, and so on. Accordingly, in some instances, electronic devices operated by the one or more relevant parties may be in communication with the platform.

A user 112, such as the one or more relevant parties, may access online platform 100 through a web based software application or browser. The web based software application may be embodied as, for example, but not be limited to, a website, a web application, a desktop application, and a mobile application compatible with a computing device 1000.

Figure 2:
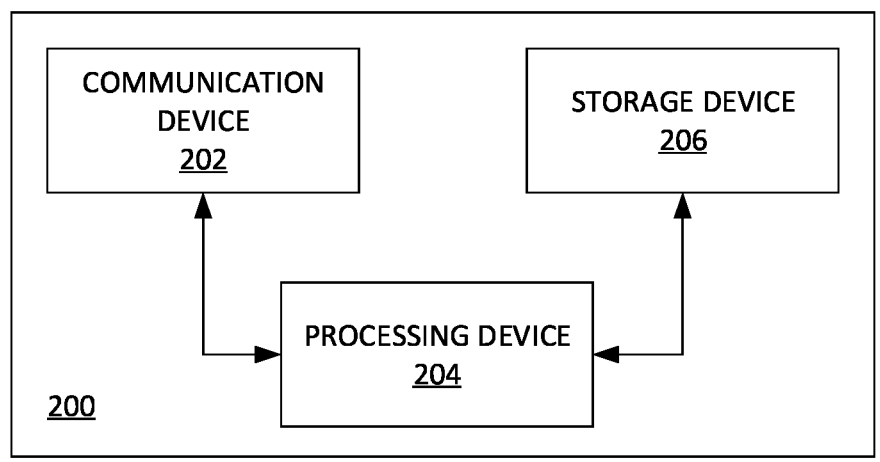
FIG. 2 is a block diagram of a clinical decision support system for predicting a diagnosis of musculoskeletal pathologies, in accordance with some embodiments.

FIG. 2 is a block diagram of a clinical decision support system 200 for predicting a diagnosis of musculoskeletal pathologies, in accordance with some embodiments. Accordingly, the clinical decision support system 200 may include a communication device 202, a processing device 204, and a storage device 206. Further, the communication device 202 may be configured for transmitting a plurality of questions associated with a musculoskeletal system of a body to at least one first device. Further, the plurality of questions may be formulated based on an affected region of the body. Further, the communication device 202 may be configured for receiving a plurality of responses corresponding to the plurality of questions from the at least one first device. Further, the plurality of responses may include at least one indication of musculoskeletal pain and/or a clinical presentation (signs) and/or a symptom associated with at least one portion of the body. Further, the communication device 202 may be configured for transmitting a prediction to at least one second device. Further, the at least one first device may be operated by at least one individual. Further, the at least one first device may be operated by at least one medical practitioner. Further, the at least one medical practitioner may include a doctor, a nurse, a clinician, etc.

Further, the processing device 204 may be communicatively coupled with the communication device 202. Further, the processing device 204 may be configured for analyzing the plurality of responses based on a knowledge repository. Further, the processing device 204 may be configured for generating the prediction of a diagnosis of at least one musculoskeletal pathology using at least one machine learning model based on the analyzing. Further, in an instance, the diagnosis may include a differential diagnosis.

Further, the storage device 206 may be communicatively coupled with the processing device 204. Further, the storage device 206 may be configured for retrieving the knowledge repository.

Further, in some embodiments, the processing device 204 may be configured for generating a plurality of first questions based on the analyzing of the plurality of responses corresponding to the plurality of questions. Further, the processing device 204 may be configured for analyzing a plurality of first responses corresponding to the plurality of first questions based on the knowledge repository. Further, the generating of the prediction of the diagnosis may be based on the analyzing of the plurality of first responses. Further, the communication device 202 may be further configured for transmitting the plurality of first questions to the at least one first device. Further, the communication device 202 may be configured for receiving the plurality of first responses corresponding to the plurality of first questions from the at least one first device.

Further, in some embodiments, the communication device 202 may be configured for transmitting a plurality of response options corresponding to each question of the plurality of questions to the at least one first device. Further, each response of the plurality of responses may include a response option indication corresponding to a response option of the plurality of response options.

Further, in some embodiments, the at least one first device may include at least one imaging sensor. Further, the at least one imaging sensor may be configured for generating at least one body layout data of the body. Further, the at least one body layout data may include at least one of a position and an orientation of at least one element of the musculoskeletal system. Further, the plurality of responses may include the at least one body layout data. Further, the at least one element of the musculoskeletal system may include at least one bone of a skeleton, at least one muscle, at least one cartilage, at least one tendon, at least one ligament, at least one joint, at least one connective tissue, etc.

Further, in some embodiments, the at least one body layout data may include at least one reference point indication and at least two selected point indications. Further, the processing device 204 may be configured for identifying at least one reference point and at least two selected points of the musculoskeletal system based on the analyzing. Further, the at least one reference point and the at least two selected points may include the at least one element. Further, the processing device 204 may be configured for determining an angle between the at least two selected points using the at least one reference point based on the analyzing and the identifying. Further, the generating of the prediction of the diagnosis may be based on the determining of the angle.

Further, in some embodiments, the at least one body layout data may include the at least one reference point indication and at least one selected point indication. Further, the processing device 204 may be configured for identifying at least one reference point and at least one selected point of the musculoskeletal system based on the analyzing. Further, the at least one reference point and the at least one selected point may include the at least one element. Further, the processing device 204 may be configured for determining at least one movement of the at least one selected point in relation to the at least one reference point based on the analyzing and the identifying. Further, the generating of the prediction of the diagnosis may be based on the determining of the at least one movement.

Further, in some embodiments, the at least one body layout data may include a plurality of points of the musculoskeletal system. Further, the plurality of points may be associated with at least one arrangement corresponding to at least one posture of the body. Further, the processing device 204 may be configured for comparing the plurality of points based on a plurality of standard points of the musculoskeletal system. Further, the plurality of standard points may be associated with at least one standard arrangement corresponding to a standard posture of the body. Further, the processing device 204 may be configured for generating a posture deviation based on the comparing. Further, the communication device 202 may be configured for transmitting the posture deviation to the at least one second device.

Further, in some embodiments, the analyzing may include performing discriminant analysis of the plurality of responses. Further, the analyzing may include determining at least one result based on the performing. Further, the analyzing may include matching the at least one result with at least one clinical condition comprised in the knowledge repository. Further, the analyzing may include identifying at least one clinical hypothesis based on the matching.

Further, in some embodiments, the processing device 204 may be configured for transforming the plurality of responses based on a clinical note format. Further, the processing device 204 may be configured for generating a clinical note based on the transforming. Further, the communication device 202 may be further configured for transmitting the clinical note to the at least one second device.

Further, in some embodiments, the knowledge repository may include a plurality of clinical conditions and a plurality of clinical hypotheses modeled as a set of 'if-then rules' and a set of certainty factors. Further, modeling of the plurality of clinical conditions and the plurality of clinical hypotheses allows ruling of a clinical hypothesis corresponding to a clinical condition. Further, the modeling allows generating a probability for the ruling of the clinical hypothesis corresponding to the clinical condition.

Figure 3:
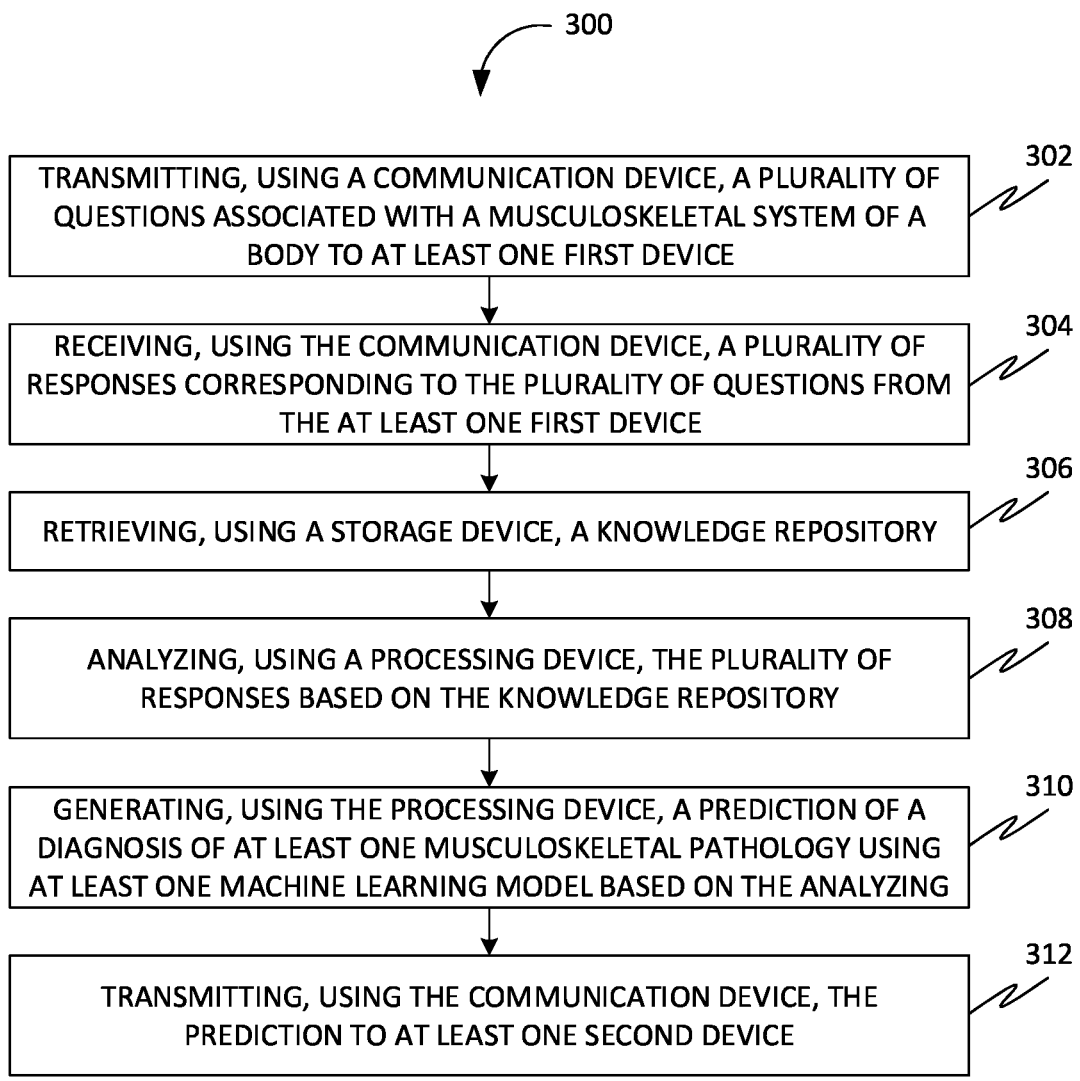
FIG. 3 is a flowchart of a method for providing clinical decision support for predicting a diagnosis of musculoskeletal pathologies, in accordance with some embodiments.

FIG. 3 is a flowchart of a method 300 for providing clinical decision support for predicting a diagnosis of musculoskeletal pathologies and spine related pathologies in particular, in accordance with some embodiments. Accordingly, at 302, the method 300 may include transmitting, using a communication device, a plurality of questions associated with a musculoskeletal system of a body to at least one first device. Further, the plurality of questions may be formulated based on an affected region of the body. Further, the at least one first device may be operated by at least one individual. Further, the at least one first device may be operated by at least one medical practitioner. Further, the at least one medical practitioner may include a doctor, a nurse, a clinician, etc.

Further, at 304, the method 300 may include receiving, using the communication device, a plurality of responses corresponding to the plurality of questions from the at least one first device. Further, the plurality of responses may include at least one indication of musculoskeletal pain and/or a clinical presentation (signs) and/or a symptom associated with at least one portion of the body.

Further, at 306, the method 300 may include retrieving, using a storage device, a knowledge repository. Further, the knowledge repository may include a plurality of clinical conditions and a plurality of clinical hypotheses modeled as a set of 'if-then rules' and a set of certainty factors. Further, modeling of the plurality of clinical conditions and the plurality of clinical hypotheses allows ruling of differential diagnosis corresponding to the clinical presentation. Further, the modeling allows generating a probability for the ruling of the clinical hypothesis corresponding to the clinical condition.

Further, at 308, the method 300 may include analyzing, using a processing device, the plurality of responses based on the knowledge repository.

Further, at 310, the method 300 may include generating, using the processing device, a prediction of a diagnosis of at least one musculoskeletal pathology using at least one machine learning model based on the analyzing. Further, in an instance, the diagnosis may include a differential diagnosis.

Further, at 312, the method 300 may include transmitting, using the communication device, the prediction to at least one second device.

Further, the analyzing may include performing discriminant analysis of the plurality of responses. Further, the analyzing may include determining at least one result based on the performing. Further, the analyzing may include matching the at least one result with at least one clinical condition comprised in the knowledge repository. Further, the analyzing may include identifying at least one clinical hypothesis based on the matching.

In further embodiments, the method 300 may include transmitting, using the communication device, a plurality of response options corresponding to each question of the plurality of questions to the at least one first device. Further, each response of the plurality of responses may include a response option indication corresponding to a response option of the plurality of response options.

Further, the at least one first device may include at least one imaging sensor. Further, the at least one imaging sensor may be configured for generating at least one body layout data of the body. Further, the at least one body layout data may include at least one of a position and an orientation of at least one element of the musculoskeletal system. Further, the plurality of responses may include the at least one body layout data.

Figure 4:
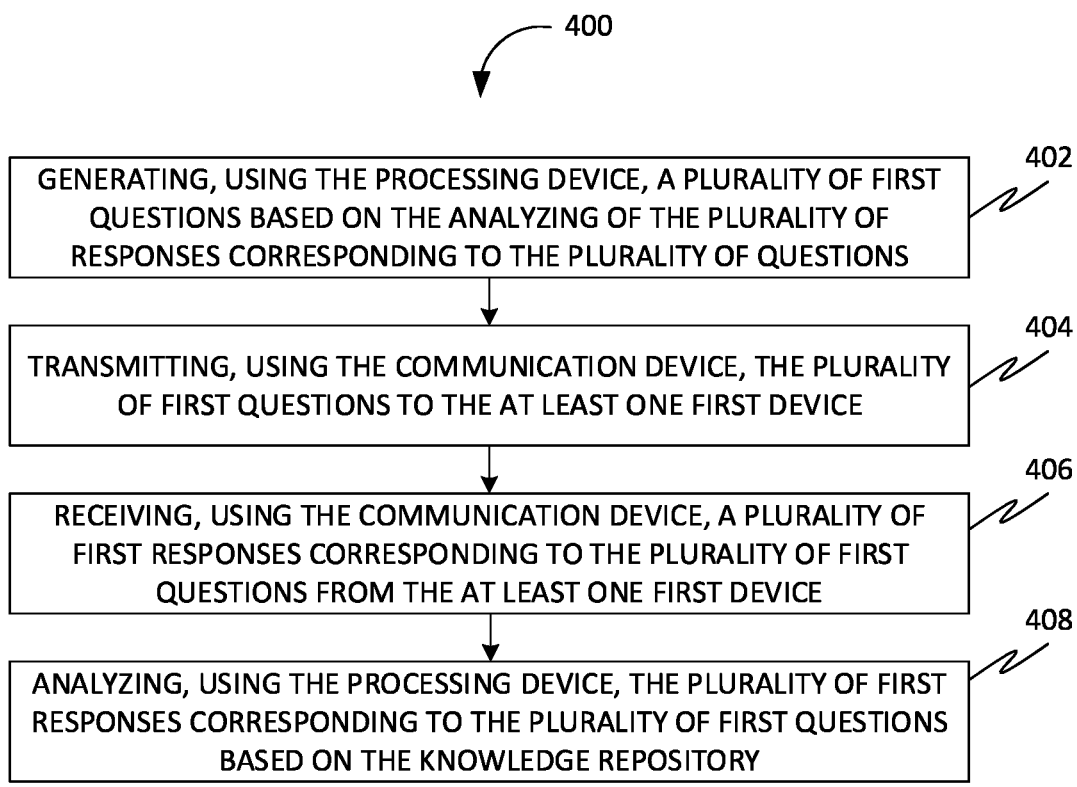
FIG. 4 is a flowchart of a method for generating the prediction of the diagnosis, in accordance with some embodiments.

FIG. 4 is a flowchart of a method 400 for generating the prediction of the diagnosis, in accordance with some embodiments. Accordingly, at 402, the method 400 may include generating, using the processing device, a plurality of first questions based on the analyzing of the plurality of responses corresponding to the plurality of questions.

Further, at 404, the method 400 may include transmitting, using the communication device, the plurality of first questions to the at least one first device.

Further, at 406, the method 400 may include receiving, using the communication device, a plurality of first responses corresponding to the plurality of first questions from the at least one first device.

Further, at 408, the method 400 may include analyzing, using the processing device, the plurality of first responses corresponding to the plurality of first questions based on the knowledge repository. Further, the generating of the prediction of the diagnosis may be based on the analyzing of the plurality of first responses.

Figure 5:
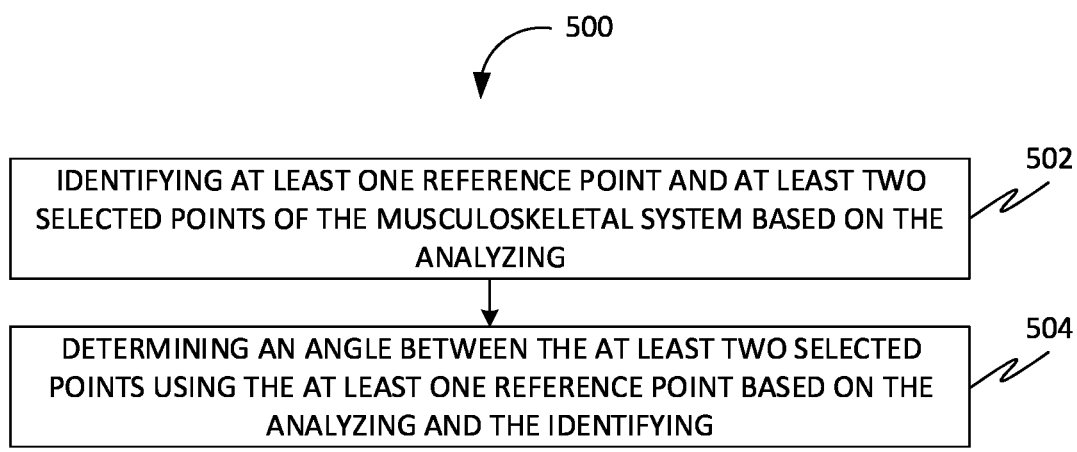
FIG. 5 is a flowchart of a method for determining an angle between at least two selected points, in accordance with some embodiments.

FIG. 5 is a flowchart of a method 500 for determining an angle between at least two selected points, in accordance with some embodiments. Accordingly, the at least one body layout data may include at least one reference point indication and at least two selected point indications. Further, at 502, the method 500 may include identifying, using the processing device, at least one reference point and at least two selected points of the musculoskeletal system based on the analyzing. Further, the at least one reference point and the at least two selected points may include the at least one element.

Further, at 504, the method 500 may include determining, using the processing device, an angle between the at least two selected points using the at least one reference point based on the analyzing and the identifying. Further, the generating of the prediction of the diagnosis may be based on the determining of the angle.

Figure 6:
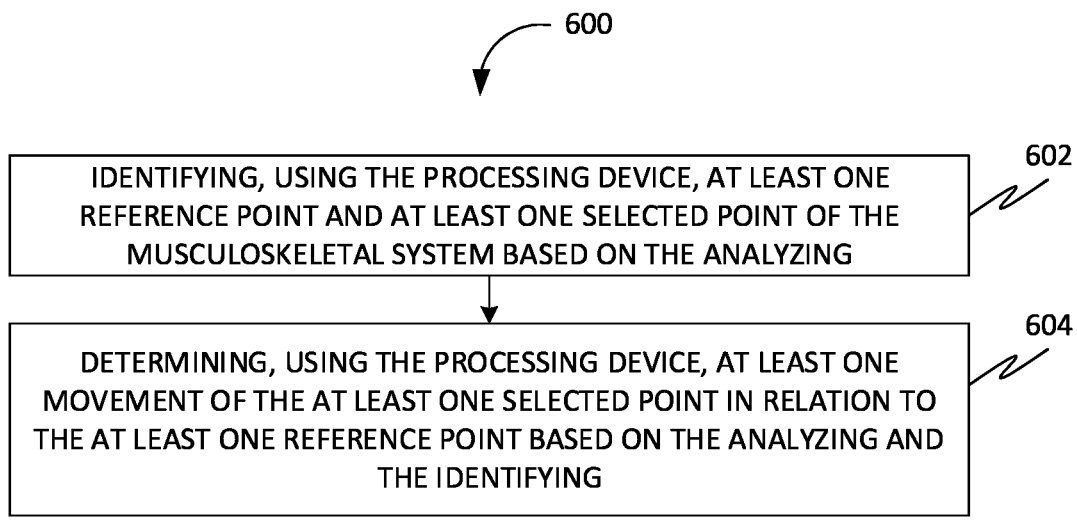
FIG. 6 is a flowchart of a method for determining at least one movement, in accordance with some embodiments.

FIG. 6 is a flowchart of a method 600 for determining at least one movement, in accordance with some embodiments. Accordingly, the at least one body layout data may include the at least one reference point indication and at least one selected point indication.

Further, at 602, the method 600 may include identifying, using the processing device, at least one reference point and at least one selected point of the musculoskeletal system based on the analyzing. Further, the at least one reference point and the at least one selected point may include the at least one element.

Further, at 604, the method 600 may include determining, using the processing device, at least one movement of the at least one selected point in relation to the at least one reference point based on the analyzing and the identifying. Further, the generating of the prediction of the diagnosis may be based on the determining of the at least one movement.

Figure 7:
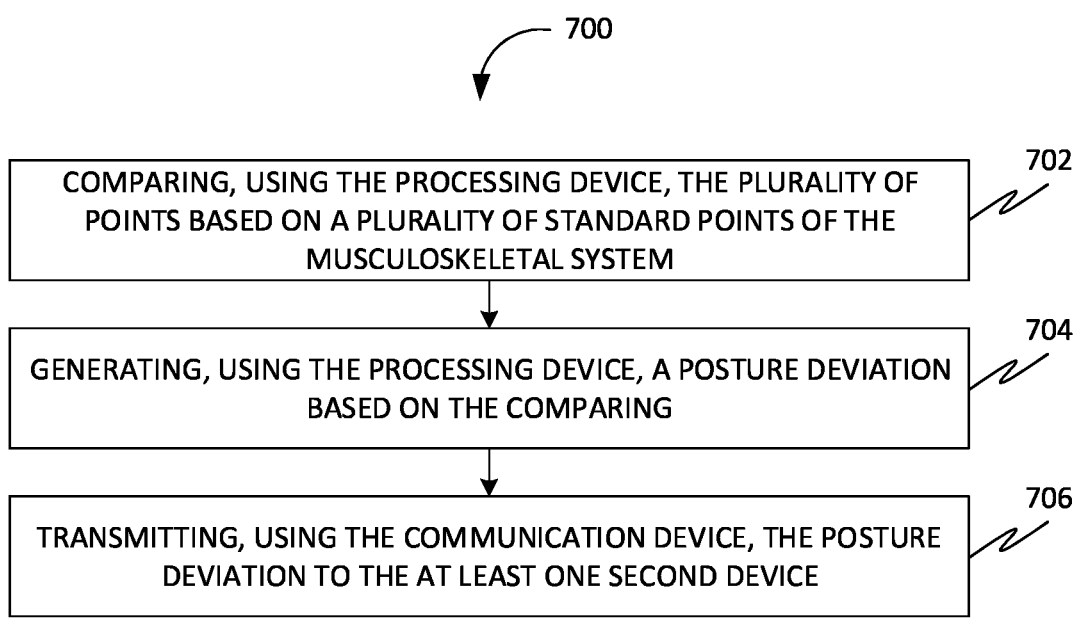
FIG. 7 is a flowchart of a method for generating a posture deviation, in accordance with some embodiments.

FIG. 7 is a flowchart of a method 700 for generating a posture deviation, in accordance with some embodiments. Accordingly, the at least one body layout data may include a plurality of points of the musculoskeletal system. Further, the plurality of points may be associated with at least one arrangement corresponding to at least one posture of the body. Further, at 702, the method 700 may include comparing, using the processing device, the plurality of points based on a plurality of standard points of the musculoskeletal system. Further, the plurality of standard points may be associated with at least one standard arrangement corresponding to a standard posture of the body.

Further, at 704, the method 700 may include generating, using the processing device, a posture deviation based on the comparing.

Further, at 706, the method 700 may include transmitting, using the communication device, the posture deviation to the at least one second device.

Figure 8:
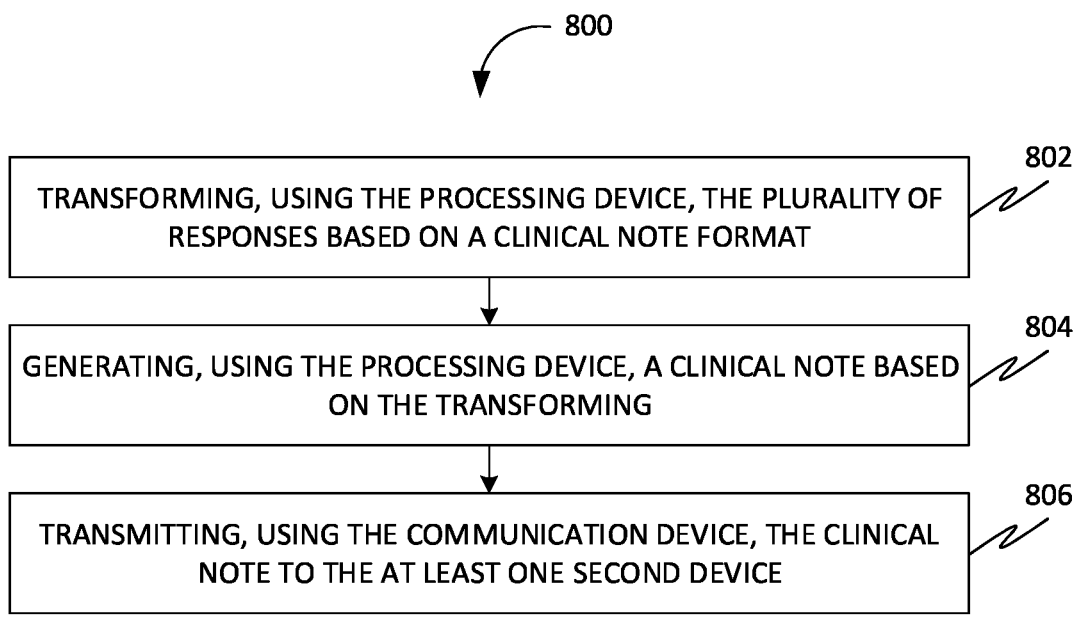
FIG. 8 is a flowchart of a method for generating a clinical note, in accordance with some embodiments.

FIG. 8 is a flowchart of a method 800 for generating a clinical note, in accordance with some embodiments. Accordingly, at 802, the method 800 may include transforming, using the processing device, the plurality of responses based on a clinical note format.

Further, at 804, the method 800 may include generating, using the processing device, a clinical note based on the transforming.

Further, at 806, the method 800 may include transmitting, using the communication device, the clinical note to the at least one second device.

Figure 9:
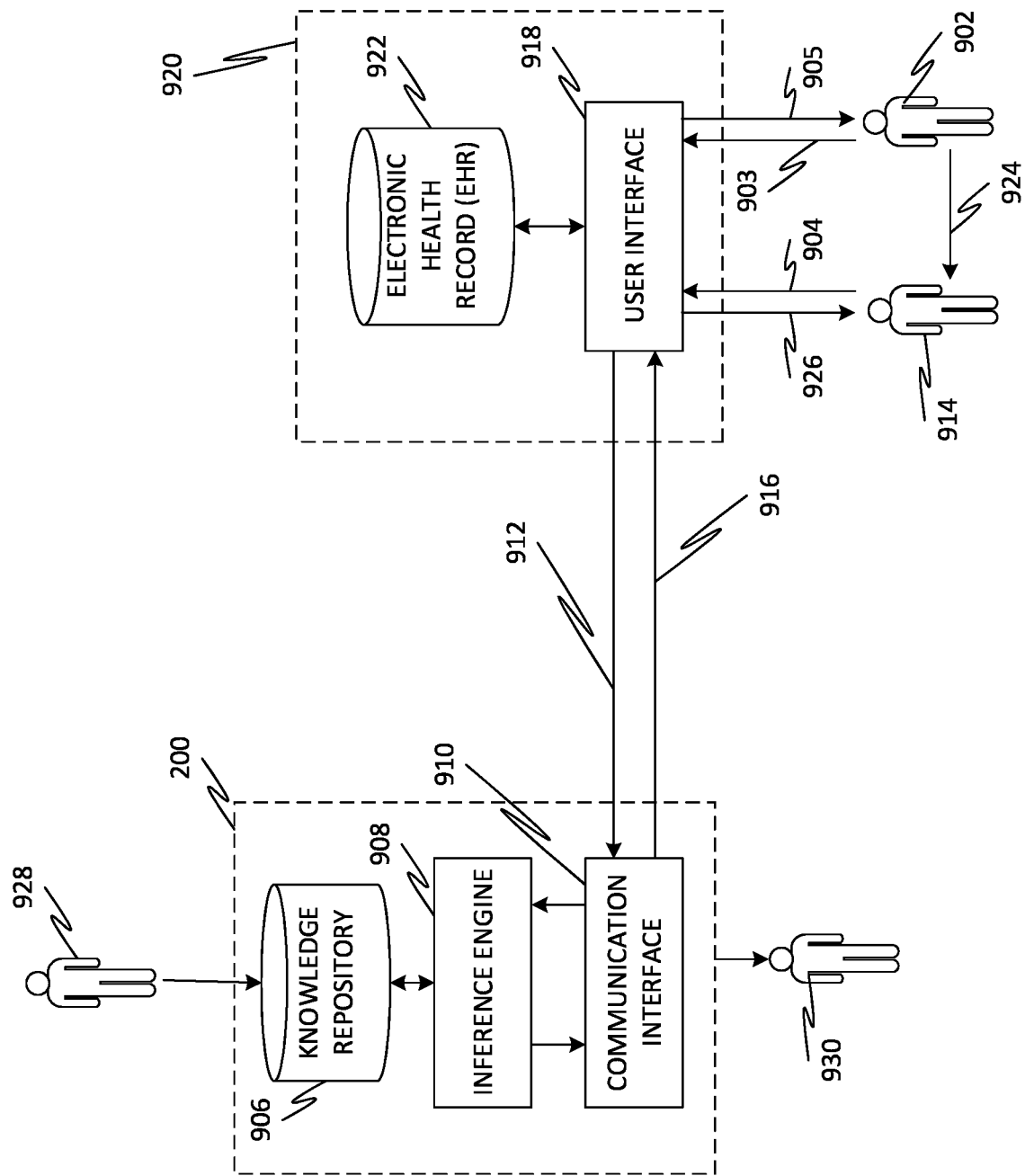
FIG. 9 is a flow diagram of the Clinical Decision Support System interacting with a Health Information System (HIS), in accordance with some embodiments.

FIG. 9 is a flow diagram of the Clinical Decision Support System 200 interacting with a Health Information System (HIS) 920, in accordance with some embodiments.

Accordingly, at 903, a patient 902 may input a patient specific data to the Health Information System (HIS) 920 using a user interface 918. Further, the Clinical Decision Support System 200 may include a knowledge repository 1006, an inference engine 908, and a communication interface 910. Further, the inference engine 908 may be configured for processing data (such as the patient specific data, a diagnostic label, etc.) based on an algorithm such as a locked algorithm. Further, at 912, the communication interface 910 may facilitate receiving of the patient specific data that may be entered by at least one of a clinician 914 and the patient 902. Further, at 916, the communication interface 910 may facilitate transmitting triage summary, clinical prediction, and clinical documentation to at least one of the patient 902 and the clinician 914 using the user interface 918. Further, the Health Information System 920 (HIS) may include an Electronic Health Record (EHR) 922 and the user interface 918. Further, at 926, the clinician 914 may request assistance from the Clinical Decision Support System 200 and perform at least one of view and edit subject data using the user interface 918. Further, at 926, the clinician 914 may receive a report based on input by the patient 902. Further, the clinician 914 may edit his input and request for any update. Further, the subject data may be associated with the patient specific data. Further, at 924, the clinician 914 may perform one on one visit with the patient 902. Further, at 904, the clinician 914 may access output (such as the clinical prediction and the clinical documentation) received from the CDSS 200 using the user interface 918. Further, at 905, the patient 902 may receive the triage summary and clinical summary that may be received from the CDSS 200 using the user interface 918. Further, knowledge experts 928 may provide the diagnostic label utilizing a classification system integrated into the knowledge repository 1006. Further, providing the diagnostic label may train the Clinical Decision Support System 200 based on supervised learning. Further, the knowledge experts 928 may include clinical experts, health information and technology experts, Machine Learning (ML) experts, and implementation experts. Further, a system analyst 930 may perform testing and validation for a decision model associated with the Clinical Decision Support System 200.

Figure 10:
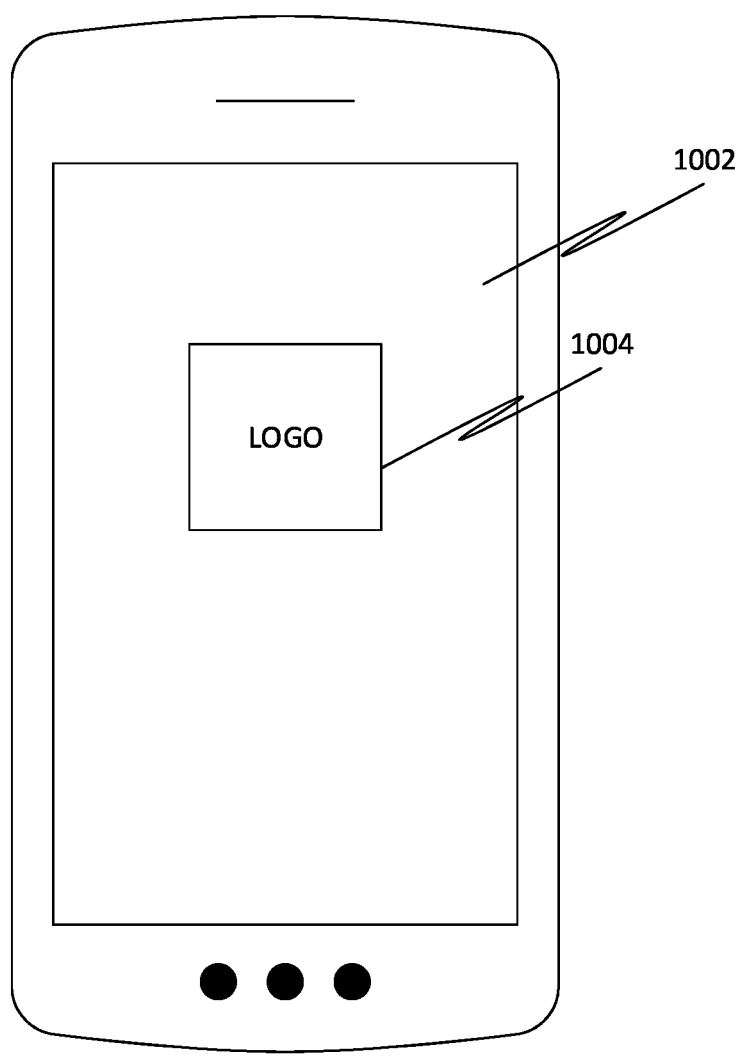
FIG. 10 is a snapshot of a user interface of a software application associated with the Clinical Decision Support System, in accordance with some embodiments.

FIG. 10 is a snapshot of a user interface 1002 of a software application associated with the Clinical Decision Support System 200, in accordance with some embodiments. Accordingly, the user interface 1002 may include an opening screen (or a home screen). Further, the opening screen may include a logo 1004. Further, the opening screen may include an opening message. Further, the logo 1004 may be associated with the ProGonio.

Figure 11:
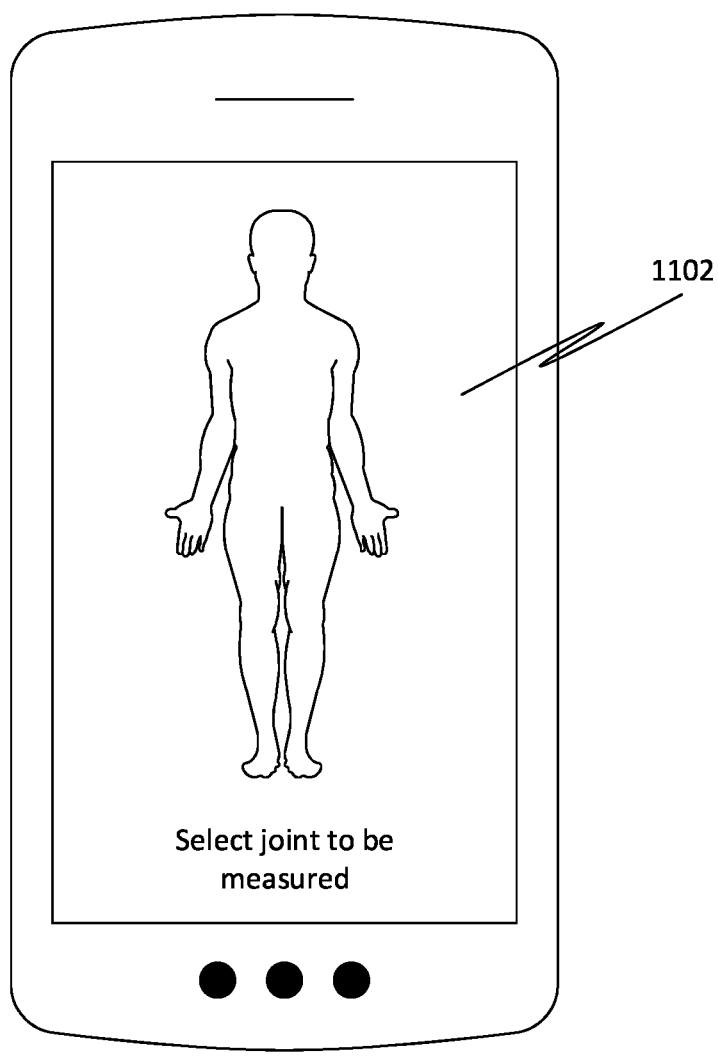
FIG. 11 is a snapshot of a joint selection user interface of the software application associated with the Clinical Decision Support System, in accordance with some embodiments.

FIG. 11 is a snapshot of a joint selection user interface 1102 of the software application associated with the Clinical Decision Support System 200, in accordance with some embodiments. Accordingly, the joint selection user interface 1102 may facilitate selection of a joint that may be measured by the user. Further, the joint selection user interface 1102 may display a full diagram of a full body of the user.

Figure 12:
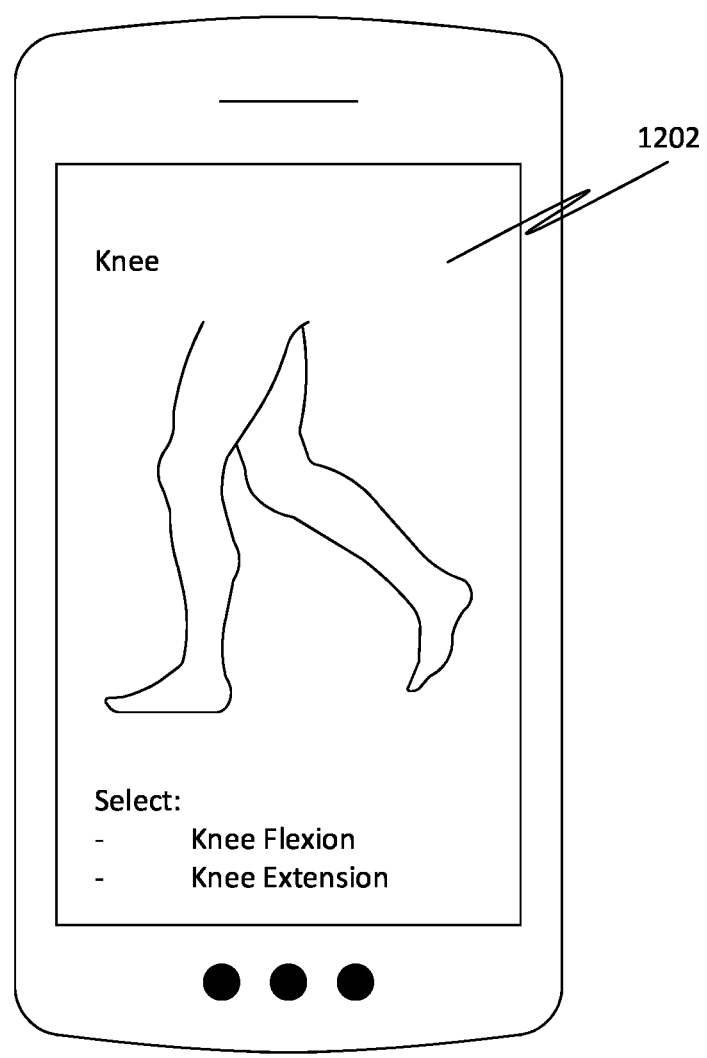
FIG. 12 is a snapshot of a user interface of the software application associated with the Clinical Decision Support System, in accordance with some embodiments.

FIG. 12 is a snapshot of a user interface 1202 of the software application associated with the Clinical Decision Support System 200, in accordance with some embodiments. Accordingly, the user interface 1202 may display an enlarged view of the joint that may be selected by the user. Further, the user interface 1202 may display a selection list of a plurality of degrees of freedom for the joint that may be selected by the user. Further, upon selection of the joint that the user may not want to measure, the user interface 1202 may include an option that may return the user to the joint selection user interface 1102. Further, the user interface 1202 may include an option that may provide information associated with the joint that may be measured by the user. Further, the information may include type of joint, normal range of motion, and movements of the joint.

Figure 13:
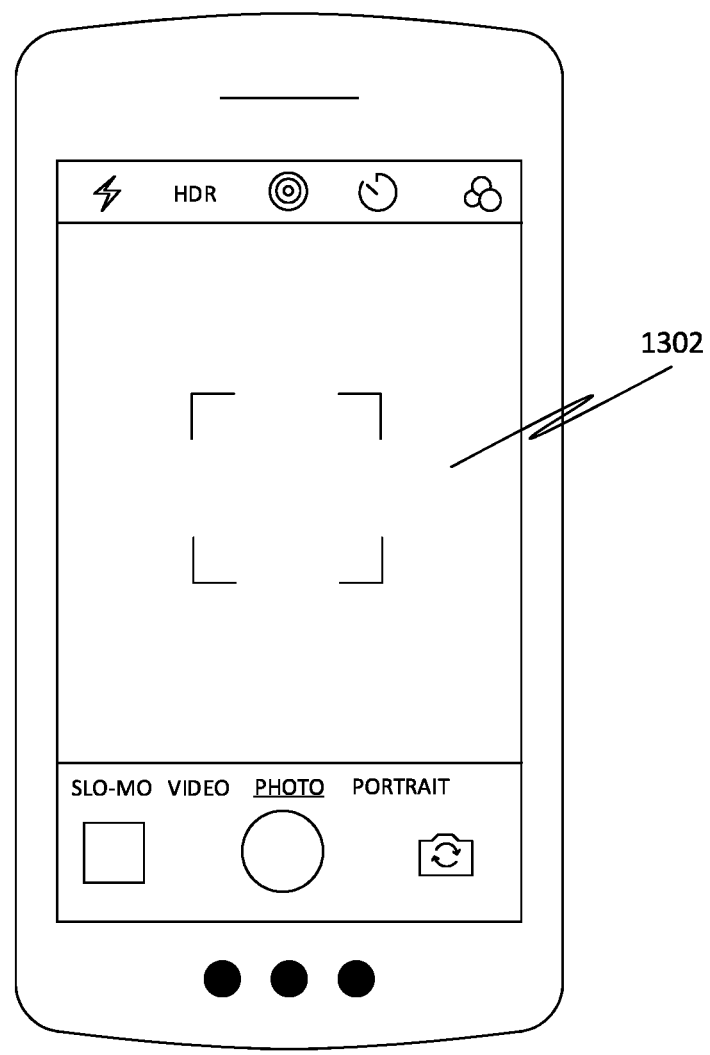
FIG. 13 is a snapshot of a motion user interface of the software application associated with the Clinical Decision Support System, in accordance with some embodiments.

FIG. 13 is a snapshot of a motion user interface 1302 of the software application associated with the Clinical Decision Support System 200, in accordance with some embodiments. Accordingly, the motion user interface 1302 may provide an option to place reference points associated with the joint manually by the user. Further, the motion user interface 1302 may display a measured value associated with the joint. Further, the software application may include an additional user interface that may proceed to the motion user interface 1302. Further, the additional user interface may provide instructions for holding and using a camera associated with the Clinical Decision Support System 200. Further, the camera may be functional in one of portrait orientation and landscape orientation.

Figure 14:
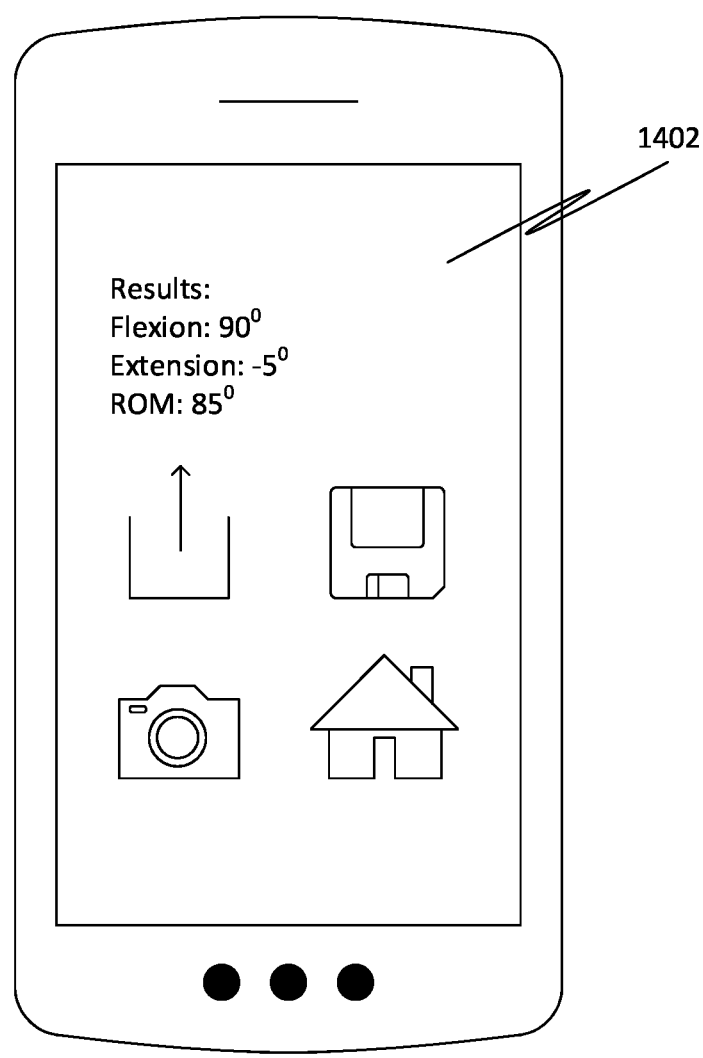
FIG. 14 is a snapshot of a result user interface of the software application associated with the Clinical Decision Support System, in accordance with some embodiments.

FIG. 14 is a snapshot of a result user interface 1402 of the software application associated with the Clinical Decision Support System 200, in accordance with some embodiments. Accordingly, the result user interface 1402 may display results associated with the range of motion of the joint. Further, the result user interface 1402 may provide options for performing at least one function. Further, the at least one function may include saving the results, sending the results, returning to the camera (or the motion user interface 1302), and returning to the home screen (or the user interface 1002). Further, the result user interface 1402 may display measurements associated with a session of measuring the joint. For instance, the joint may include a knee. Further, the result user interface 1402 may display a value of extension and value of flexion for the knee.

Figure 15:
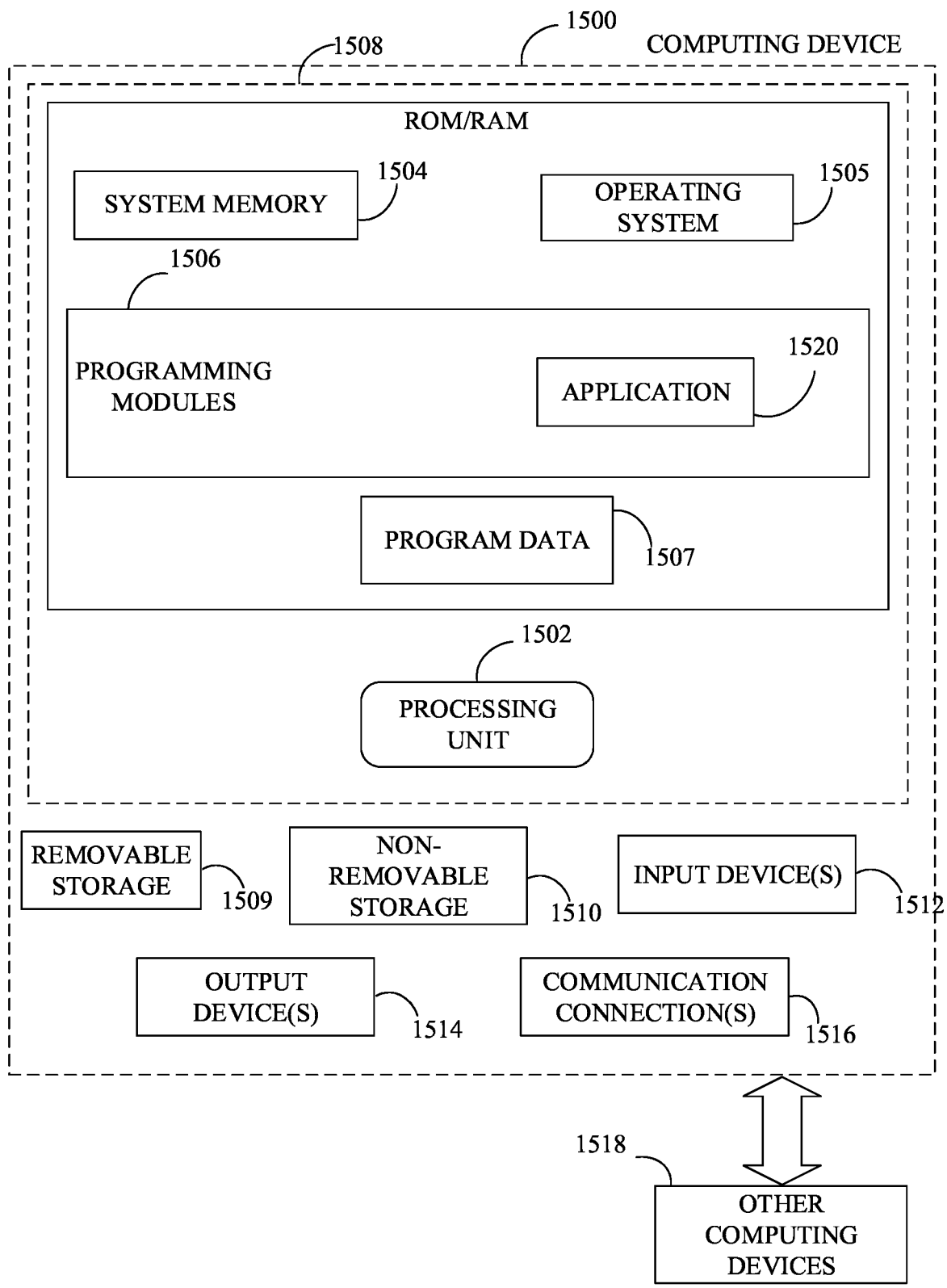
FIG. 15 is a block diagram of a computing device for implementing the methods disclosed herein, in accordance with some embodiments

With reference to FIG. 15, a system consistent with an embodiment of the disclosure may include a computing device or cloud service, such as computing device 1500. In a basic configuration, computing device 1500 may include at least one processing unit 1502 and a system memory 1504. Depending on the configuration and type of computing device, system memory 1504 may comprise, but is not limited to, volatile (e.g. random-access memory (RAM)), non-volatile (e.g. read-only memory (ROM)), flash memory, or any combination. System memory 1504 may include operating system 1505, one or more programming modules 1506, and may include a program data 1507. Operating system 1505, for example, may be suitable for controlling computing device 1500's operation. In one embodiment, programming modules 1506 may include image-processing module, machine learning module. Furthermore, embodiments of the disclosure may be practiced in conjunction with a graphics library, other operating systems, or any other application program and is not limited to any particular application or system. This basic configuration is illustrated in FIG. 15 by those components within a dashed line 1508.

Computing device 1500 may have additional features or functionality. For example, computing device 1500 may also include additional data storage devices (removable and/or non-removable) such as, for example, magnetic disks, optical disks, or tape. Such additional storage is illustrated in FIG. 15 by a removable storage 1509 and a non-removable storage 1510. Computer storage media may include volatile and non-volatile, removable and non-removable media implemented in any method or technology for storage of information, such as computer-readable instructions, data structures, program modules, or other data. System memory 1504, removable storage 1509, and non-removable storage 1510 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1500. Any such computer storage media may be part of device 1500. Computing device 1500 may also have input device(s) 1512 such as a keyboard, a mouse, a pen, a sound input device, a touch input device, a location sensor, a camera, a biometric sensor, etc. Output device(s) 1514 such as a display, speakers, a printer, etc. may also be included. The aforementioned devices are examples and others may be used.

Computing device 1500 may also contain a communication connection 1516 that may allow device 1500 to communicate with other computing devices 1518, such as over a network in a distributed computing environment, for example, an intranet or the Internet. Communication connection 1516 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 1504, including operating system 1505. While executing on processing unit 1502, programming modules 1506 (e.g., application 1520) may perform processes including, for example, one or more stages of methods, algorithms, systems, applications, servers, databases as described above. The aforementioned process is an example, and processing unit 1502 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

REFERENCES

[1] Fall Detection Based on Key Points of Human-Skeleton Using OpenPose by Weiming Chen, Zijie Jiang, Hailin Guo and Xiaoyang Ni *Faculty of Engineering, China University of Geosciences (Wuhan), Wuhan 430074, China; chenweiming@cug.edu.cn (W. C.); jzj0803@ foxmail.com (Z. J.); hl_guo2004@163.com (H. G.):

[2] Design Process and Utilization of a Novel Clinical Decision Support System for Neuropathic Pain in Primary Care: Mixed Methods Observational Study Dale Guenter, Mohamed Abouzahra, Inge Schabort, Arun Radhakrishnan, Kalpana Nair, Sherrie Orr, Jessica Langevin, Paul Taenzer, Dwight E Moulin JMIR Med Inform. 2019 July-September; 7(3): e14141. Published online 2019 Sep. 30. DOI: 10.2196/14141 PMCID: PMC6792030

[3] "A patient like me"—An algorithm-based program to inform patients on the likely conditions people with symptoms like theirs have. Koren G, Souroujon D, Shaul R, Bloch A, Leventhal A, Lockett J, Shalev V Medicine (Baltimore). 2019 October; 98(42):e17596. DOI: 10.1097/MD.0000000000017596.

[4] Clinical Decision Support Tools for Selecting Interventions for Patients with Disabling Musculoskeletal Disorders: A Scoping Review. Douglas P. Gross, Susan Armijo-Olivo, William S. Shaw, Kelly Williams-Whitt, Nicola T. Shaw, Jan Hartvigsen, Ziling Qin, Christine Ha, Linda J. Woodhouse, Ivan A. Steenstra. J Occup Rehabil. 2016; 26: 286-318. Published online 2015 Dec. 14. DOI: 10.1007/s10926-015-9614-1 PMCID: PMC4967425

[5] Effects of Documentation Based Decision Support on Chronic Disease Management, ajmc, 2010; 16:

[6] Dieleman J L, Cao J, Chapin A, et al. US Health Care Spending by Payer and Health Condition, 1996-2016. JAMA. 2020; 323(9):863-884. DOI:10.1001/jama.2020.0734

[7] Institute of Medicine (US) and National Academy of Engineering (US) Roundtable on Value & Science-Driven Health Care. Engineering a Learning Healthcare System: A Look at the Future. Washington (D.C.): National Academies Press (US); 2011.

[8] Mroz T E, Lubelski D, Williams S K, et al. Differences in the surgical treatment of recurrent lumbar disc herniation among spine surgeons in the United States. Spine J. 2014; 14(10):2334-2343. DOI:10.1016/j.spinee.2014.01.037

[9] Gillis J. The history of the patient history since 1850. Bull Hist Med. 2006; 80(3):490-512. DOI:10.1353/bhm.2006.0097

[10] New Data on Musculoskeletal Disease Highlight its Position as Major Contributor to Health Care Costs, https://www.apta.org/PTinMotion/News/2018/01/23/USBJIMusculoskeletalBurden/[11]

[11] Insurance coverage, costs, and barriers to care for outpatient musculoskeletal therapy and rehabilitation services. E Carvalho, J P Bettger . . . —North Carolina medical . . . , 2017—ncmedicaljournal.com. http://www.ncmedicaljournal.com/content/78/5/312.full

[12] Gillis J. The history of the patient history since 1850. Bull Hist Med. 2006; 80(3):490-512. doi:10.1353/bhm.2006.0097 and Summerton N. The medical history as a diagnostic technology. Br J Gen Pract. 2008; 58(549): 273-276. doi:10.3399/bjgp08X279779
[13] Druzdzel, M. J., & Flynn, R. R. (2009). Decision Support Systems. Encyclopedia of Library and Information Sciences, Third Edition, 1458-1466. doi:10.1081/e-elis3-120043887
[14] Kannan A, Fries J A, Kramer E, Chen J J, Shah N, Amatriain X. The accuracy vs. coverage trade-off in patient-facing diagnosis models. AMIA Jt Summits Transl Sci Proc. 2020 May 30; 2020:298-307. PMID: 32477649; PMCID: PMC7233065.
[15] Gupta P. K. et al. (2020) Overview of Clinical Decision Support System (CDSS) as a Computational Tool and Its Applications in Public Health. In: Kumar R, Paiva S. (eds) Applications in Ubiquitous Computing. EAI/Springer Innovations in Communication and Computing. Springer, Cham. https://doi.org/10.1007/978-3-030-35280-6_5
[16] Secure and Robust Machine Learning for Healthcare: A Survey 2020 https://arxiv.org/abs/2001.08103
[17] Sendak, M. P., Gao, M., Brajer, N., & Balu, S. (2020). Presenting machine learning model information to clinical end users with model facts labels. Npj Digital Medicine, 3(1), 1-4. https://doi.org/10.1038/s41746-020-0253-3

The invention claimed is:

1. A clinical decision support system for predicting a diagnosis of musculoskeletal pathologies, the clinical decision support system comprising:
   a communication device configured for:
      transmitting a plurality of questions associated with a musculoskeletal system of a body to at least one first device, wherein the plurality of questions is formulated based on an affected region of the body;
      receiving a plurality of responses corresponding to the plurality of questions from the at least one first device, wherein the plurality of responses comprises at least one indication of a symptom associated with at least one portion of the body; and
      transmitting a prediction to at least one second device;
   a processing device communicatively coupled with the communication device, wherein the processing device is configured for:
      analyzing the plurality of responses based on a knowledge repository; and
      generating the prediction of a diagnosis of at least one musculoskeletal pathology using at least one machine learning model based on the analyzing; and
   a storage device communicatively coupled with the processing device, wherein the storage device is configured for retrieving the knowledge repository;
   wherein the at least one first device comprises at least one imaging sensor, wherein the at least one imaging sensor is configured for generating at least one body layout data of the body, wherein the at least one body layout data comprises at least one of a position and an orientation of at least one element of the musculoskeletal system, wherein the plurality of responses comprises the at least one body layout data;
   wherein the at least one body layout data comprises at least one reference point indication and at least two selected point indications;
   wherein the processing device is further configured for:
      identifying at least one reference point and at least two selected points of the musculoskeletal system based on the analyzing, wherein the at least one reference point and the at least two selected points comprises the at least one element; and
      determining an angle between the at least two selected points using the at least one reference point based on the analyzing and the identifying, wherein the generating of the prediction of the diagnosis is based on the determining of the angle.

2. The clinical decision support system of claim 1, wherein the processing device is further configured for:
   generating a plurality of first questions based on the analyzing of the plurality of responses corresponding to the plurality of questions; and
   analyzing a plurality of first responses corresponding to the plurality of first questions based on the knowledge repository, wherein the generating of the prediction of the diagnosis is based on the analyzing of the plurality of first responses, wherein the communication device is further configured for:
   transmitting the plurality of first questions to the at least one first device; and
   receiving the plurality of first responses corresponding to the plurality of first questions from the at least one first device.

3. The clinical decision support system of claim 1, wherein the communication device is further configured for transmitting a plurality of response options corresponding to each question of the plurality of questions to the at least one first device, wherein each response of the plurality of responses comprises a response option indication corresponding to a response option of the plurality of response options.

4. The clinical decision support system of claim 1, wherein the at least one body layout data comprises at least one reference point indication and at least one selected point indication, wherein the processing device is further configured for:
   identifying at least one reference point and at least one selected point of the musculoskeletal system based on the analyzing, wherein the at least one reference point and the at least one selected point comprises the at least one element; and
   determining at least one movement of the at least one selected point in relation to the at least one reference point based on the analyzing and the identifying, wherein the generating of the prediction of the diagnosis is based on the determining of the at least one movement.

5. The clinical decision support system of claim 1, wherein the at least one body layout data comprises a plurality of points of the musculoskeletal system, wherein the plurality of points is associated with at least one arrangement corresponding to at least one posture of the body, wherein the processing device is configured for:
   comparing the plurality of points based on a plurality of standard points of the musculoskeletal system, wherein the plurality of standard points is associated with at least one standard arrangement corresponding to a standard posture of the body; and
   generating a posture deviation based on the comparing, wherein the communication device is further configured for transmitting the posture deviation to the at least one second device.

6. The clinical decision support system of claim 1, wherein the analyzing comprises:
   performing discriminant analysis of the plurality of responses;
   determining at least one result based on the performing;
   matching the at least one result with at least one clinical condition comprised in the knowledge repository; and identifying at least one clinical hypothesis based on the matching.

7. The clinical decision support system of claim 1, wherein the processing device is further configured for:
transforming the plurality of responses based on a clinical note format; and
generating a clinical note based on the transforming, wherein the communication device is further configured for transmitting the clinical note to the at least one second device.

8. The clinical decision support system of claim 1, wherein the knowledge repository comprises a plurality of clinical conditions and a plurality of clinical hypotheses modeled as a set of 'if-then rules' and a set of certainty factors, wherein modeling of the plurality of clinical conditions and the plurality of clinical hypotheses allows ruling of a clinical hypothesis corresponding to a clinical condition, wherein the modeling allows generating a probability for the ruling of the clinical hypothesis corresponding to the clinical condition.

9. A method for providing clinical decision support for predicting a diagnosis of musculoskeletal pathologies, the method comprising:
transmitting, using a communication device, a plurality of questions associated with a musculoskeletal system of a body to at least one first device, wherein the plurality of questions is formulated based on an affected region of the body;
receiving, using the communication device, a plurality of responses corresponding to the plurality of questions from the at least one first device, wherein the plurality of responses comprises at least one indication of a symptom associated with at least one portion of the body;
retrieving, using a storage device, a knowledge repository;
analyzing, using a processing device, the plurality of responses based on the knowledge repository;
generating, using the processing device, a prediction of a diagnosis of at least one musculoskeletal pathology using at least one machine learning model based on the analyzing; and
transmitting, using the communication device, the prediction to at least one second device;
wherein the at least one first device comprises at least one imaging sensor, wherein the at least one imaging sensor is configured for generating at least one body layout data of the body, wherein the at least one body layout data comprises at least one of a position and an orientation of at least one element of the musculoskeletal system, wherein the plurality of responses comprises the at least one body layout data;
wherein the at least one body layout data comprises at least one reference point indication and at least two selected point indications;
wherein the method further comprises:
identifying, using the processing device, at least one reference point and at least two selected points of the musculoskeletal system based on the analyzing, wherein the at least one reference point and the at least two selected points comprises the at least one element; and
determining, using the processing device, an angle between the at least two selected points using the at least one reference point based on the analyzing and the identifying, wherein the generating of the prediction of the diagnosis is based on the determining of the angle.

10. The method of claim 9 further comprising:
generating, using the processing device, a plurality of first questions based on the analyzing of the plurality of responses corresponding to the plurality of questions;
transmitting, using the communication device, the plurality of first questions to the at least one first device;
receiving, using the communication device, a plurality of first responses corresponding to the plurality of first questions from the at least one first device; and
analyzing, using the processing device, the plurality of first responses corresponding to the plurality of first questions based on the knowledge repository, wherein the generating of the prediction of the diagnosis is based on the analyzing of the plurality of first responses.

11. The method of claim 9 further comprising transmitting, using the communication device, a plurality of response options corresponding to each question of the plurality of questions to the at least one first device, wherein each response of the plurality of responses comprises a response option indication corresponding to a response option of the plurality of response options.

12. The method of claim 9, wherein the at least one body layout data comprises at least one reference point indication and at least one selected point indication, wherein the method further comprises:
identifying, using the processing device, at least one reference point and at least one selected point of the musculoskeletal system based on the analyzing, wherein the at least one reference point and the at least one selected point comprises the at least one element; and
determining, using the processing device, at least one movement of the at least one selected point in relation to the at least one reference point based on the analyzing and the identifying, wherein the generating of the prediction of the diagnosis is based on the determining of the at least one movement.

13. The method of claim 9, wherein the at least one body layout data comprises a plurality of points of the musculoskeletal system, wherein the plurality of points is associated with at least one arrangement corresponding to at least one posture of the body, wherein the method further comprises:
comparing, using the processing device, the plurality of points based on a plurality of standard points of the musculoskeletal system, wherein the plurality of standard points is associated with at least one standard arrangement corresponding to a standard posture of the body;
generating, using the processing device, a posture deviation based on the comparing; and
transmitting, using the communication device, the posture deviation to the at least one second device.

14. The method of claim 9, wherein the analyzing comprises:
performing discriminant analysis of the plurality of responses;
determining at least one result based on the performing;
matching the at least one result with at least one clinical condition comprised in the knowledge repository; and
identifying at least one clinical hypothesis based on the matching.

15. The method of claim 9 further comprising:
transforming, using the processing device, the plurality of responses based on a clinical note format;
generating, using the processing device, a clinical note based on the transforming; and
transmitting, using the communication device, the clinical note to the at least one second device.

16. The method of claim 9, wherein the knowledge repository comprises a plurality of clinical conditions and a plurality of clinical hypotheses modeled as a set of 'if-then rules' and a set of certainty factors, wherein modeling of the plurality of clinical conditions and the plurality of clinical hypotheses allows ruling of a clinical hypothesis corresponding to a clinical condition, wherein the modeling allows generating a probability for the ruling of the clinical hypothesis corresponding to the clinical condition.

* * * * *